United States Patent
Gysling et al.

(10) Patent No.: US 7,152,460 B2
(45) Date of Patent: *Dec. 26, 2006

(54) APPARATUS AND METHOD FOR COMPENSATING A CORIOLIS METER

(75) Inventors: Daniel L. Gysling, Glastonbury, CT (US); Patrick Curry, Glastonbury, CT (US); Douglas H. Loose, Southington, CT (US); Thomas E. Banach, Barkhamsted, CT (US)

(73) Assignee: Cidra Corporation, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/892,886

(22) Filed: Jul. 15, 2004

(65) Prior Publication Data

US 2005/0044929 A1 Mar. 3, 2005

Related U.S. Application Data

(60) Provisional application No. 60/579,448, filed on Jun. 14, 2004, provisional application No. 60/570,321, filed on May 21, 2004, provisional application No. 60/539,640, filed on Jan. 28, 2004, provisional application No. 60/524,964, filed on Nov. 25, 2003, provisional application No. 60/512,794, filed on Oct. 20, 2003, provisional application No. 60/510,302, filed on Oct. 10, 2003, provisional application No. 60/504,785, filed on Sep. 22, 2003, provisional application No. 60/503,334, filed on Sep. 16, 2003, provisional application No. 60/491,860, filed on Aug. 1, 2003, provisional application No. 60/487,832, filed on Jul. 15, 2003.

(51) Int. Cl.
*G01N 7/00* (2006.01)
*G01N 22/00* (2006.01)
*G01F 1/20* (2006.01)

(52) U.S. Cl. .................. 73/32 A; 73/861.18; 73/61.44

(58) Field of Classification Search ............... 73/61.44, 73/61.45, 61.47, 61.49, 61.78, 61.79, 861.04, 73/861.08, 32 A, 861.18

See application file for complete search history.

(56) References Cited

U.S. PATENT DOCUMENTS 2,874,568 A  2/1959  Petermann (Continued)

FOREIGN PATENT DOCUMENTS

EP        222503 A1  *  5/1987

(Continued)

OTHER PUBLICATIONS

"Noise and Vibration Control Engineering Principles and Applications", Leo L. Bernaek and Istvan L. Ver, A. Wiley Interscience Publication, pp. 537-541, Aug. 1992.

(Continued)

*Primary Examiner*—Hezron Williams
*Assistant Examiner*—John Fitzgerald

(57) ABSTRACT

A flow measuring system is provided that provides at least one of a compensated mass flow rate measurement and a compensated density measurement. The flow measuring system includes a gas volume fraction meter in combination with a coriolis meter. The GVF meter measures acoustic pressures propagating through the fluids to measure the speed of sound $\alpha_{mix}$ propagating through the fluid to calculate at least gas volume fraction of the fluid and/or the reduced natural frequency. For determining an improved density for the coriolis meter, the calculated gas volume fraction and/or reduced frequency is provided to a processing unit. The improved density is determined using analytically derived or empirically derived density calibration models (or formulas derived therefore), which is a function of the measured natural frequency and at least one of the determined GVF, reduced frequency and speed of sound, or any combination thereof. The gas volume fraction (GVF) meter may include a sensing device having a plurality of strain-based or pressure sensors spaced axially along the pipe for measuring the acoustic pressures propagating through the flow.

64 Claims, 14 Drawing Sheets

U.S. PATENT DOCUMENTS

| | | | |
|---|---|---|---|
| 3,444,723 A * | 5/1969 | Wakefield | 73/32 A |
| 3,780,577 A * | 12/1973 | Brown | 73/861.28 |
| 4,004,461 A | 1/1977 | Lynnworth | |
| 4,048,853 A | 9/1977 | Smith et al. | 73/861.25 |
| 4,080,837 A | 3/1978 | Alexander et al. | 73/61.45 |
| 4,144,754 A * | 3/1979 | Pitts et al. | 73/861.02 |
| 4,195,517 A | 4/1980 | Kalinoski et al. | |
| 4,248,085 A | 2/1981 | Coulthard | 73/861.06 |
| 4,262,523 A * | 4/1981 | Stansfeld | 73/24.05 |
| 4,445,389 A | 5/1984 | Potzick et al. | 73/861.27 |
| 4,580,444 A * | 4/1986 | Abts et al. | 73/61.75 |
| 4,773,257 A * | 9/1988 | Aslesen et al. | 73/61.44 |
| 4,823,613 A * | 4/1989 | Cage et al. | 73/861.355 |
| 4,896,540 A | 1/1990 | Shakkottai et al. | 73/861.02 |
| 5,029,482 A | 7/1991 | Liu et al. | 73/861.04 |
| 5,040,415 A | 8/1991 | Barkhoudarian | 073/861.03 |
| 5,083,452 A | 1/1992 | Hope | 73/61 R |
| 5,218,197 A | 6/1993 | Carroll | 250/227.19 |
| 5,224,372 A | 7/1993 | Kolpak et al. | |
| 5,259,239 A * | 11/1993 | Gaisford | 73/61.44 |
| 5,285,675 A | 2/1994 | Colgate et al. | 73/23.2 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,594,180 A | 1/1997 | Carpenter et al. | 73/861.356 |
| 5,654,502 A * | 8/1997 | Dutton | 73/152.18 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,856,622 A | 1/1999 | Yamamoto et al. | |
| 5,948,959 A | 9/1999 | Peloquin | 73/1.83 |
| 6,016,702 A | 1/2000 | Maron | |
| 6,065,328 A * | 5/2000 | Dayton et al. | 73/25.01 |
| 6,151,958 A | 11/2000 | Letton et al. | 73/61.79 |
| 6,202,494 B1 | 3/2001 | Ricbel et al. | 73/861.29 |
| 6,318,156 B1 * | 11/2001 | Dutton et al. | 73/61.44 |
| 6,335,959 B1 * | 1/2002 | Lynch et al. | 378/45 |
| 6,354,147 B1 | 3/2002 | Gysling et al. | 73/61.79 |
| 6,378,357 B1 | 4/2002 | Han et al. | 73/54.41 |
| 6,397,683 B1 | 6/2002 | Hagenmeyer et al. | |
| 6,401,538 B1 * | 6/2002 | Han et al. | 73/599 |
| 6,422,092 B1 * | 7/2002 | Morrison et al. | 73/861.04 |
| 6,435,030 B1 | 8/2002 | Gysling et al. | 73/587 |
| 6,450,037 B1 | 9/2002 | Davis et al. | |
| 6,463,813 B1 | 10/2002 | Gysling | 73/862.59 |
| 6,502,465 B1 * | 1/2003 | Vedapuri et al. | 73/861.04 |
| 6,502,466 B1 * | 1/2003 | Cage et al. | 73/861.355 |
| 6,532,827 B1 | 3/2003 | Ohnishi | |
| 6,536,291 B1 | 3/2003 | Gysling et al. | 73/861.42 |
| 6,550,342 B1 | 4/2003 | Croteau et al. | 73/800 |
| 6,575,043 B1 * | 6/2003 | Huang et al. | 73/861.25 |
| 6,587,798 B1 | 7/2003 | Kersey et al. | 702/50 |
| 6,601,458 B1 | 8/2003 | Gysling et al. | 73/861.04 |
| 6,609,069 B1 | 8/2003 | Gysling | 702/48 |
| 6,672,163 B1 * | 1/2004 | Han et al. | 73/597 |
| 6,691,584 B1 | 2/2004 | Gysling et al. | 73/861.42 |
| 6,698,297 B1 | 3/2004 | Gysling | |
| 6,732,575 B1 | 5/2004 | Gysling et al. | 73/61.79 |
| 6,745,135 B1 * | 6/2004 | Keilty et al. | 702/45 |
| 6,763,698 B1 * | 7/2004 | Greenwood | 73/30.01 |
| 6,782,150 B1 | 8/2004 | Davis et al. | 385/12 |
| 6,802,224 B1 * | 10/2004 | Nakao et al. | 73/861.354 |
| 6,813,962 B1 | 11/2004 | Gysling et al. | 73/861.26 |
| 6,817,229 B1 * | 11/2004 | Han et al. | 73/64.53 |
| 6,837,098 B1 | 1/2005 | Gysling et al. | 73/61.79 |
| 6,945,095 B1 * | 9/2005 | Johansen | 73/61.44 |
| 6,950,760 B1 | 9/2005 | Henry et al. | |
| 6,971,259 B1 | 12/2005 | Gysling | |
| 7,059,199 B1 | 6/2006 | Mattar et al. | 73/861.356 |
| 2001/0045134 A1 | 11/2001 | Henry et al. | 73/861.356 |
| 2002/123852 A1 | 9/2002 | Gysling et al. | |
| 2002/0129662 A1 | 9/2002 | Gysling et al. | |
| 2003/0089161 A1 | 5/2003 | Gysling | |
| 2003/0136186 A1 | 7/2003 | Gysling et al. | |
| 2004/0069069 A1 | 4/2004 | Croteau | |
| 2004/0074312 A1 * | 4/2004 | Gysling | 73/861.04 |
| 2004/0139791 A1 * | 7/2004 | Johansen | 73/61.44 |
| 2004/0144182 A1 | 7/2004 | Gysling et al. | |
| 2004/0167735 A1 | 8/2004 | Gysling et al. | |
| 2004/0168522 A1 * | 9/2004 | Fernald et al. | 73/861.01 |
| 2004/0194539 A1 | 10/2004 | Gysling | |
| 2004/0199340 A1 | 10/2004 | Gysling et al. | |
| 2004/0199341 A1 | 10/2004 | Gysling et al. | |
| 2004/0210404 A1 | 10/2004 | Gysling et al. | |
| 2004/0216509 A1 * | 11/2004 | Antonijevic | 73/1.16 |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0011284 A1 | 1/2005 | Davis et al. | |
| 2005/0039520 A1 | 2/2005 | Bailey et al. | |
| 2005/0044966 A1 | 3/2005 | Croteau et al. | |
| 2005/0050956 A1 | 3/2005 | Croteau et al. | |
| 2005/0061060 A1 | 3/2005 | Banach et al. | |
| 2005/0072216 A1 * | 4/2005 | Engel | 73/53.01 |
| 2005/0120799 A1 * | 6/2005 | Gysling et al. | 73/753 |
| 2005/0138993 A1 * | 6/2005 | Mattar et al. | 73/61.78 |
| 2005/0171710 A1 | 8/2005 | Gysling et al. | |
| 2005/0188771 A1 * | 9/2005 | Lund Bo et al. | 73/861 |
| 2005/0193832 A1 * | 9/2005 | Tombs et al. | 73/861 |
| 2005/0210965 A1 * | 9/2005 | Sinha | 73/61.79 |

FOREIGN PATENT DOCUMENTS

| | | |
|---|---|---|
| EP | 253504 A1 * | 1/1988 |
| GB | 2009931 | 6/1979 |

OTHER PUBLICATIONS

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

"PVDF and Array Transducers" Author: Robert A. Day—NDTnet—Sep. 1996—vol. No. 9.

"Polymer Piezoelectric Transducer for Ultrasonic NDE" Aughors: Yoseph Bar-Cohen, Tianji Xue and Shyh-Shiuh Lih.

"Piezoelectric Polymers" ICASE Report No. 2001-43—Dec. 2001.

"Piezo Film Sensors Technical Manual" P/N 1005663-1 Rev. B Apr. 2, 1999.

Sonar-Based Volumetric Flow Meter For Pulp and Paper Applications—Daniel L. Gysling & Douglas H. Loose—Dec. 13, 2003.

Sonar-Based Volumetric Flow Meter for Chemical and Petrochemical Applications—Daniel L. Gysling & Douglas H. Loose—Feb. 14, 2003.

New Flowmeter Principle—By Walt Boyes—Flow Control Magazine—Oct. 2003 Issue.

SONAR Gets into the Flow—Daniel L. Gysling and Douglas H. Loose—Modern Process—Jan. 2004.

U.S. Appl. No. 60/445795, filed Feb. 10, 2003, Mattar et al.

U.S. Appl. No. 60/452934, filed Mar. 10, 2003, Mattar et al.

U.S. Appl. No. 60/549161, filed Mar. 3, 2004, Lansangan.

* cited by examiner

Effect of Fluid Inhomogeneity

Reduced Order Model Accounting for Compressibility and Inhomogeneity

APPARATUS AND METHOD FOR COMPENSATING A CORIOLIS METER

CROSS-REFERENCE TO RELATED PATENT APPLICATIONS

The present invention claims the benefit of U.S. Provisional Patent Application No. 60/579,448 filed Jun. 14, 2004, U.S. Provisional Patent Application No. 60/570,321 filed May 12, 2004, U.S. Provisional Patent Application No. 60/539,640 filed Jan. 28, 2004, U.S. Provisional Patent Application No. 60/524,964 filed Nov. 25, 2003, U.S. Provisional Patent Application No. 60/512,794 filed Oct. 20, 2003, U.S. Provisional Patent Application No. 60/510,302 filed Oct. 10, 2003, U.S. Provisional Patent Application No. 60/504,785 filed Sep. 22, 2003, U.S. Provisional Patent Application No. 60/503,334 filed Sep. 16, 2003, U.S. Provisional Patent Application No. 60/491,860 filed Aug. 1, 2003, U.S. Provisional Patent Application No. 60/487,832 filed Jul. 15, 2003, which are all incorporated herein by reference.

TECHNICAL FIELD

This invention relates to an apparatus for measuring the density and/or mass flow rate of a flow having entrained gas therein, and more particularly to an apparatus that measures the speed of sound propagating through the flow to determine the gas volume fraction of the flow in the process to augment or correct the density and or mass flow rate measurement of a coriolis meter.

BACKGROUND ART

Coriolis meters are widely used for industrial flow measurement, representing one of the largest and fasting growing segments in the industrial flow meter market. Coriolis meters have the reputation for high accuracy and provide mass flow and density as their basic measurements.

Since the technology was first adopted by industry beginning in the 1980's, Coriolis meters have developed the reputation as a high priced, high accuracy meter for use in high value applications—predominately within the chemical processing industry. However, despite their success, Coriolis meters have been plagued by poor performance in two-phase flows, predominately bubbly flows of gas/liquid mixtures.

Coriolis meters have two fundamental issues with aerated or bubbly flows. Firstly, bubbly flows present an operability challenge to coriolis meters. Most coriolis meters use electromagnetic drive actuators to vibrate the flow tube at it natural frequency. The meters rely on the vibrating tubes to generate the corilois forces which causes one leg of the flow tube to lag the other. The corilois forces, and hence phase lag, are ideally proportional to the mass flow through the flow tube. The tubes are typically excited at, or near a resonant frequency, and as such, the excitation forces required to maintain a specified vibration amplitude in the tubes is a strong function of the damping in the system. Single phase mixtures introduce little damping to the vibration of the bent tubes, however, the amount of damping in the system dramatically increases with the introduction of gas bubbles. As a result, more power is required to maintain vibration in the tubes in bubbly flows. Often more power is required than is available, resulting in the "stalling" of the Corilois meter.

Futhermore, coriolis meters often require significant time to adjust for the often rapid changes in flow tube resonant frequencies associated with the onset of bubbly or aerated flows. These time-delays, for which the flow tube is essentially stalled, greatly diminish the utility of coriolis meter in many applications where two phase flow and transient response are important such as batch processed. This stalling problem has been and is currently being address by many manufactures.

Secondly, multiphase flows present an accuracy challenge. The accuracy challenge presented by aerated flow regimes is that many of the fundamental assumptions associated with the principle of operation of Corilois meters become increasingly less accurate with the introduction of aerated flow. The present invention provides a means for improving the accuracy of Coriolis meters operating on all types of fluids, with particular emphasis on enhancing the accuracy for operating on two phase, bubbly flows and mixtures.

SUMMARY OF THE INVENTION

Objects of the present invention include an apparatus having a device for determining the speed of sound propagating within a fluid flow in a pipe to determine the gas volume fraction of a process fluid or flow flowing within a pipe, and augment to improve the accuracy of a density and/or mass flow rate measurement of a coriolis meter.

According to the present invention, a flow measuring system for measuring density of a fluid flowing in a pipe is provided. The flow measuring system includes a coriolis meter, a flow measuring device and a processing unit. The coriolis meter has at least one tube wherein fluid flows therethrough. The coriolis meter provides a frequency signal indicative of a natural frequency of a tube and/or phase signal indicative of a phase difference between a pair of tubes. The flow measuring device measures the speed of sound propagating through the fluid. The flow measuring device provides at least one of an SOS signal indicative of the speed of sound propagating through the fluid, a GVF signal indicative of the gas volume fraction of the fluid and a reduced frequency indicative of the reduced frequency of the fluid. The processing unit determines a compensated mass flow rate measurement in response to at least one of the SOS signal, the GVF signal and the reduced frequency signal and the phase signal, and/or determines a compensated density measurement in response to the SOS signal, the GVF signal and the reduced frequency signal and the frequency signal.

The foregoing and other objects, features and advantages of the present invention will become more apparent in light of the following detailed description of exemplary embodiments thereof.

BEST MODE FOR CARRYING OUT THE INVENTION

Coriolis meters provide a measurement of the mass flow and/or density of a fluid flow 12 passing through a pipe 14. As described in detail hereinbefore, a coriolis meter provides erroneous mass flow and density measurements in the presence of entrained gas within the fluid flow (e.g., bubbly gas). The present invention provides a means for compensating the coriolis meter to provide corrected or improved density and/or mass flow measurements.

Figure 1:
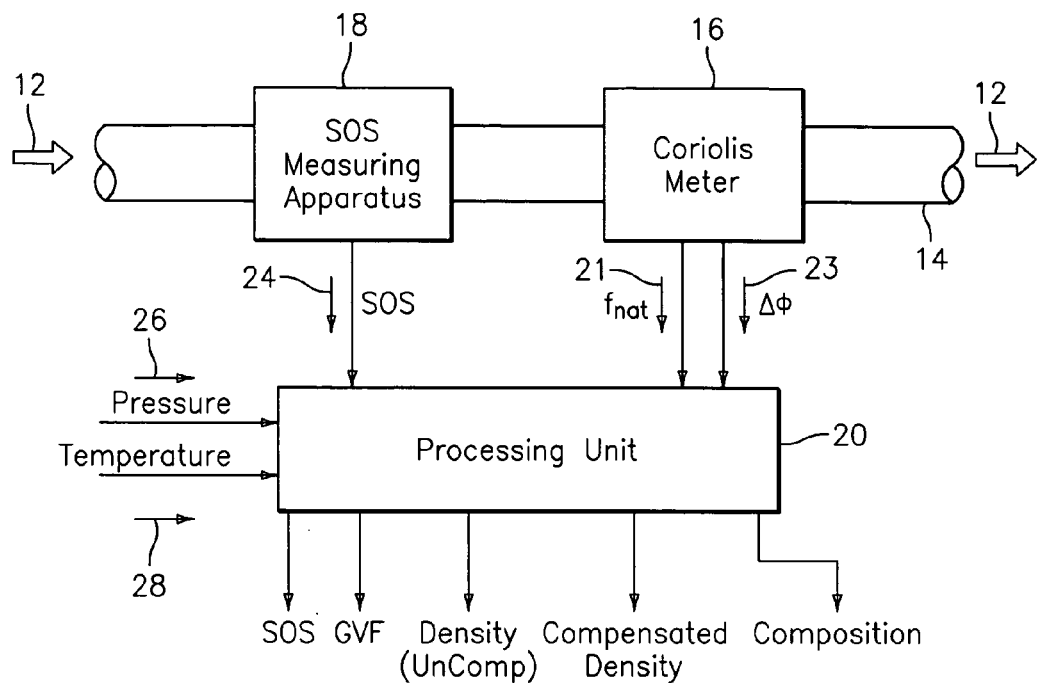
FIG. 1 is a schematic illustration of a flow measuring system for providing a density and/or mass flow rate measurement augmented for entrained gas within a fluid flow passing within a pipe, in accordance with the present invention.

As shown in FIG. 1, one embodiment of a flow measuring system 10 embodying the present invention includes a coriolis meter 16, a speed of sound (SOS) measuring apparatus 18 and a processing unit 20 to provide any one or more of the following parameters of the fluid flow, namely, gas volume fraction, speed of sound propagating through the fluid flow, uncompensated density, compensated density and composition. The fluid flow may be any aerated fluid or mixture including liquid, slurries, solid/liquid mixture, liquid/liquid mixture and any other multiphase flow.

In this embodiment, the coriolis meter 16 provides a frequency signal 22 indicative of the natural frequency of the fluid 12 loaded tubes of the coriolis meter and the phase signal 23 indicative of the phase lag in the tubes of the coriolis meter. The SOS measuring apparatus 18 provides an SOS signal 24 indicative of the speed of sound propagating through the fluid flow. A processing unit 24 processes the frequency signal, the phase signal and the SOS signal to provide at least one of the parameters of the fluid flow described hereinbefore. Pressure and/or temperature signals 26,28 may also be provided to the processing unit 20, which may be used to provide more accurate measurements of the gas volume fraction. The pressure and temperature may be measured by known means or estimated.

The coriolis meter may be any known coriolis meter, such as two inch bent tube coriolis meter manufactured my MicroMotion Inc. and a two in straight tube coriolic meter manufactured by Endress & Hauser Inc. The coriolis meters comprise a pair of bent tubes (e.g. U-shaped, pretzel shaped) or straight tubes as will be described hereinafter.

The SOS measuring device 18 includes any means for measuring the speed of sound propagating through the aerated flow 12. One method includes a pair of ultra-sonic sensors axially spaced along the pipe 14, wherein the time of flight of an ultrasonic signal propagating between an ultra-sonic transmitter and receiver. Depending on the characteristics of the flow, the frequency of the ultra-sonic signal must be relating low to reduce scatter within the flow. The meter is similar as that described in U.S. patent application Ser. No. 10/756,922 filed on Jan. 13, 2004, which is incorporated herein by reference.

Figure 2:
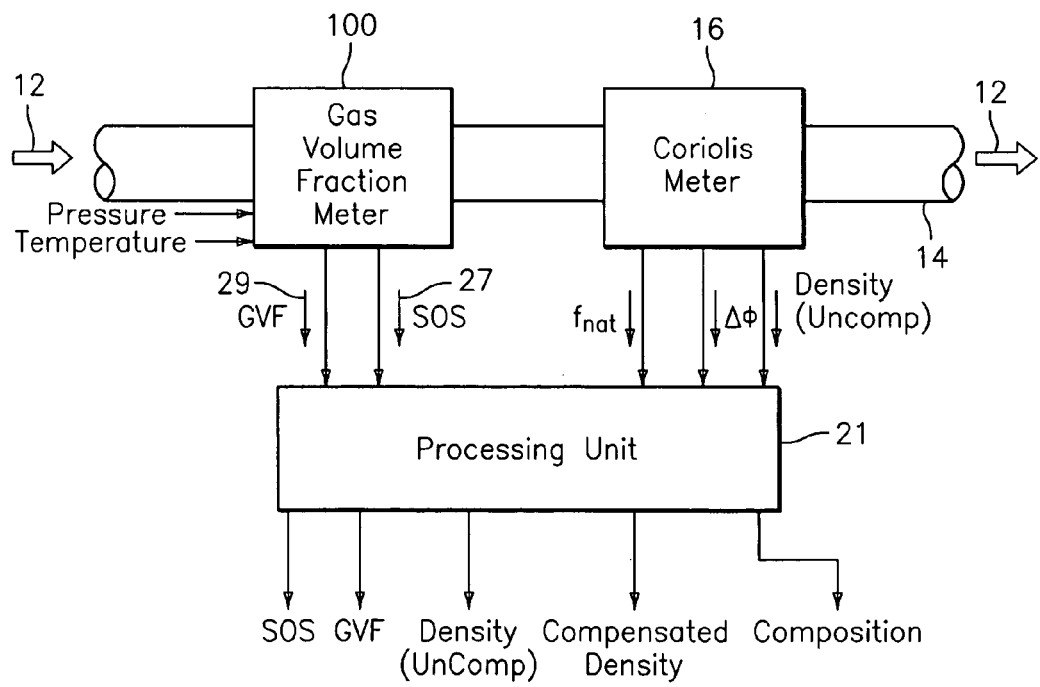
FIG. 2 is a schematic illustration of another flow measuring system for providing a density and/or mass flow rate measurement augmented for entrained gas within a fluid flow passing within a pipe, in accordance with the present invention.
Figure 20:
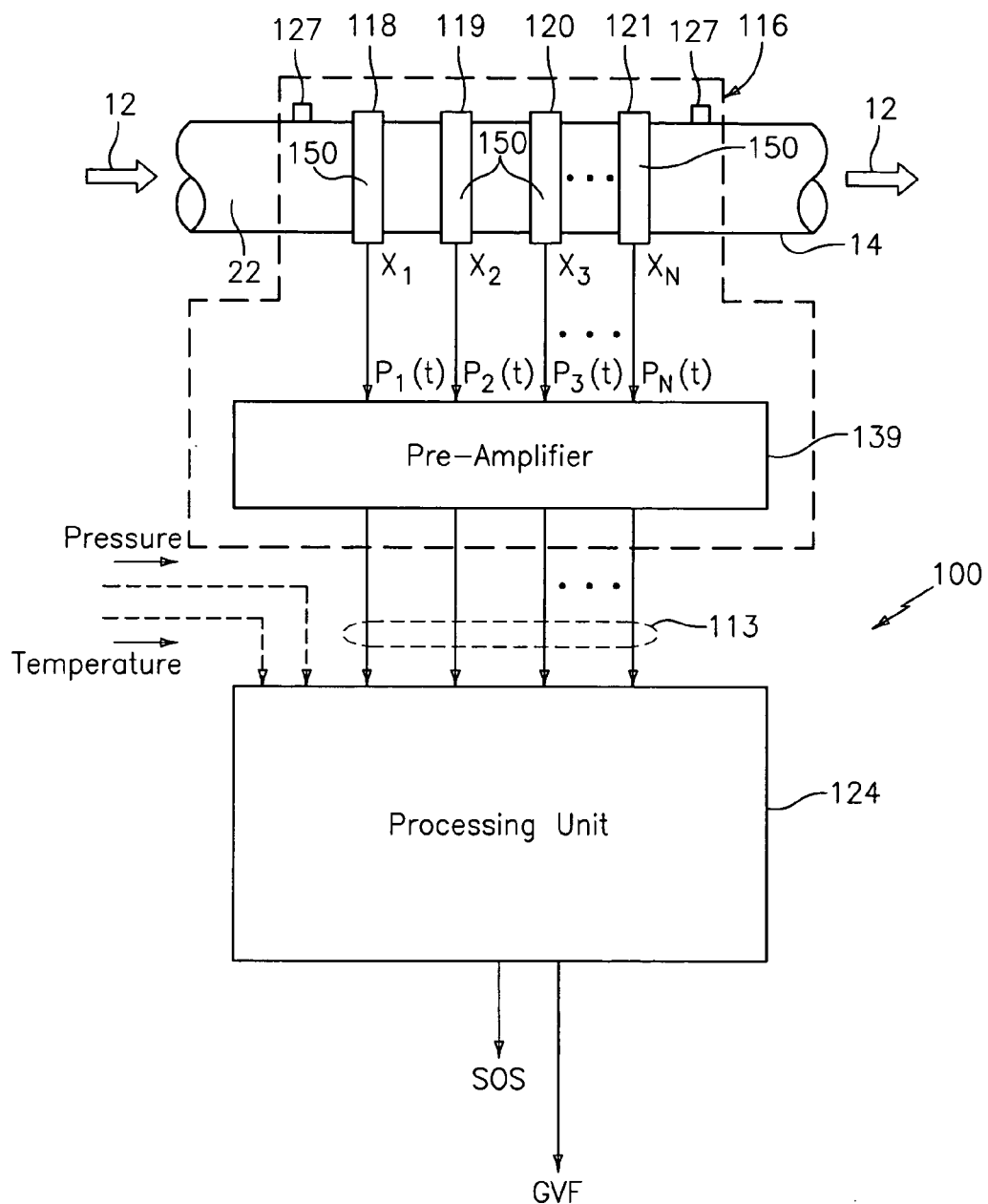
FIG. 20 is a schematic block diagram of a gas volume fraction meter, in accordance with the present invention.
Figure 21:
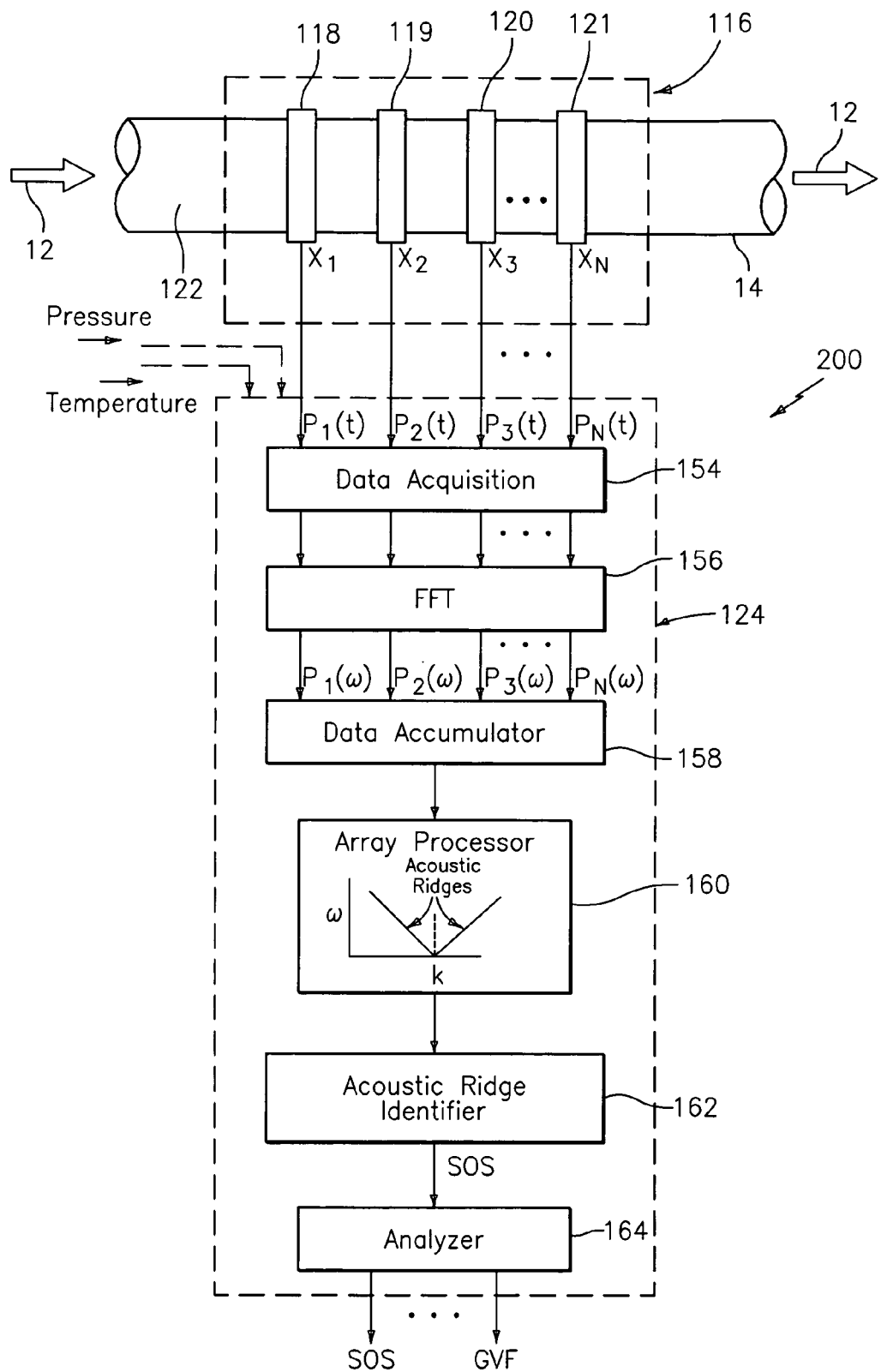
FIG. 21 is a schematic block diagram of another embodiment of gas volume fraction meter, in accordance with the present invention.

Alternatively, as shown in FIGS. 2, 20 and 21, the SOS measuring apparatus may be a gas volume fraction (GVF) meter that comprises a sensing device 116 having a plurality of strain-based or pressure sensors 118–121 spaced axially along the pipe for measuring the acoustic pressures 190 propagating through the flow 12. The GVF meter 100 determines and provides a first signal 27 indicative of the SOS in the fluid and a second signal 29 indicative of the gas volume fraction (GVF) of the flow 12, which will be described in greater detail hereinafter.

Figure 3:
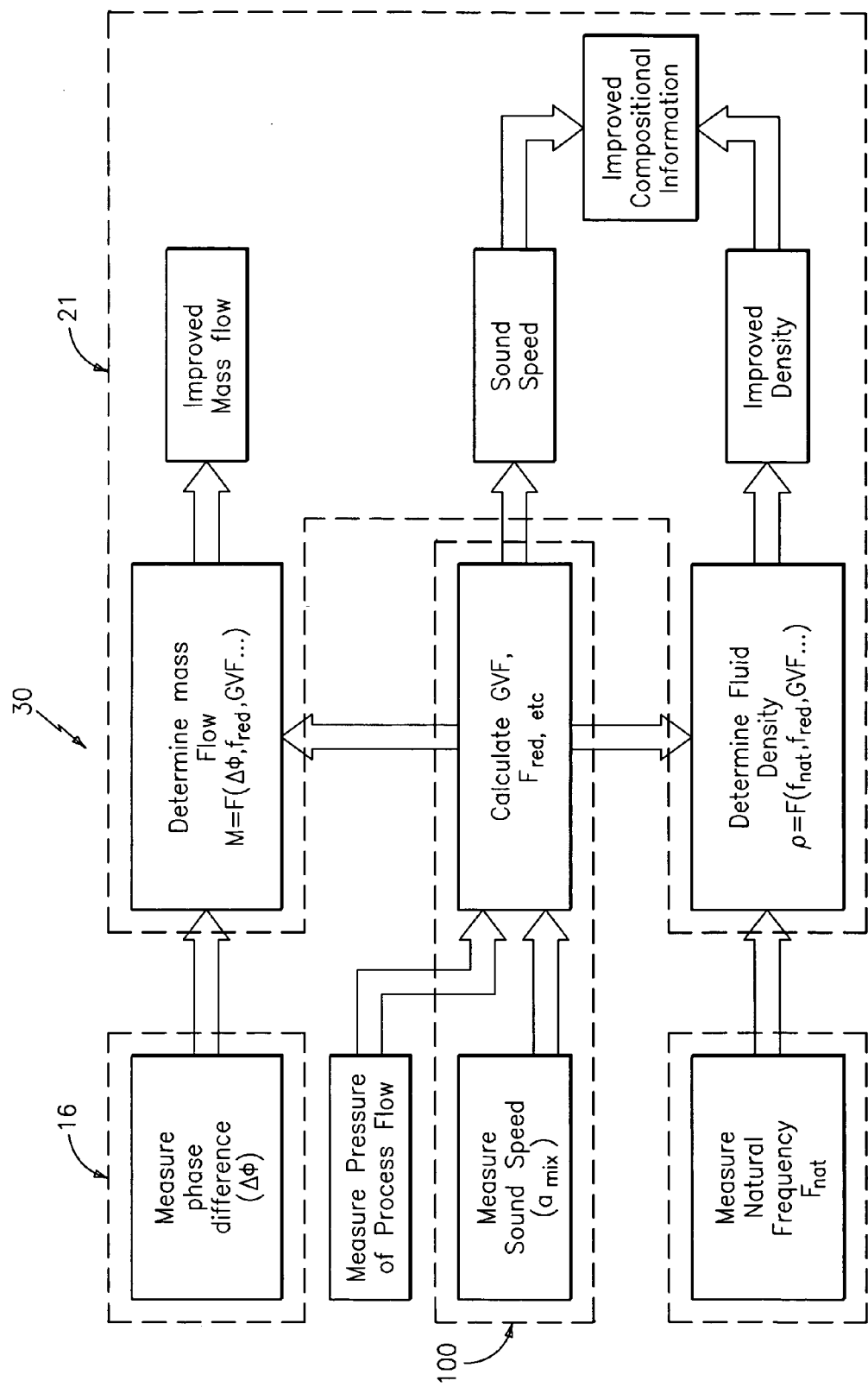
FIG. 3 is a function block diagram of a processing unit of flow measuring system similar to that of FIG. 1, in accordance with the present invention.

FIG. 3 illustrates a functional block diagram 30 of the flow measuring system of FIG. 2. As shown, the GVF meter 100 measures acoustic pressures propagating through the fluids to measure the speed of sound $a_{mix}$. The GVF meter calculates at least gas volume fraction of the fluid and/or the reduced natural frequency using the measured speed of sound. The GVF meter may also use the pressure of the process flow to determine the gas volume fraction. The pressure may be measured or estimated.

For determining an improved density for the coriolis meter, the calculated gas volume fraction and/or reduced frequency is provided to the processing unit 21. The improved density is determined using analytically derived or empirically derived density calibration models (or formulas derived therefore), which is a function of the measured natural frequency and at least one of the determined GVF, reduced frequency and speed of sound, or any combination thereof, which will be described in greater detail hereinafter. The improved density measurement is the density of the aerated flow passing through the pipe.

The present invention further contemplates determining improved compositional information of the aerated flow. In other words, knowing the speed of sound propagating through the flow and the improved density, the processing unit 21 can determine density of the fluid/mixture portion of the multiphase flow.

For example, the density ($\rho_{mix}$) of an aerated flow is related to the volumetric phase fraction of the components ($\phi_i$) and the density of the components ($\rho_i$).

$$\rho_{mix} = \sum_{i=1}^{N} \phi_i \rho_i$$

Where continuity requires:

$$\sum_{i=1}^{N} \phi_i = 1$$

The system 10 provides an improved measure of the density of the aerated flow. For a two-component mixture, knowing the density ($\rho_{gas}$), gas volume fraction (or SOS) and accurately measuring the mixture density ($\rho_{mix}$) provides a means to determine the density ($\rho_{nongas}$) of the non-gas portion of the fluid flow. For example, for a two-component fluid flow:

$$\rho_{mix} = \rho_{nongas}\phi_{nongas} + \rho_{gas}\phi_{gas}$$

therefore, $\rho_{nongas} = (\rho_{mix} - \rho_{gas}\phi_{gas})/\phi_{nongas}$, wherein $\phi_{nongas} = 1 - \phi_{gas}$ wherein $\rho_{mix}$ is the density of the mixture, $\rho_{nongas}$, $\phi_{nongas}$ are the density and phase fraction, respectively, of a non-gas component of the fluid flow, and $\rho_{gas}$, $\phi_{gas}$ are the density and phase fraction, respectively, of the entrained gas within the mixture.

Therefore, knowing the density ($\rho_{gas}$) of the gas/air, the measured gas volume fraction of the gas ($\phi_{gas}$), and the improved density measurement ($\rho_{mix}$) of the aerated flow to be compensated for entrained gas enable the density ($\rho_{nongas}$) of the non-gas portion of the aerated flow 12 to be determined, which provides improved compositional information of the aerated flow 12.

The present invention also contemplates compensating or improving the mass flow rate measurement of the coriolis meter 16, as shown in FIG. 3. For determining an improved mass flow rate for the coriolis meter, the calculated gas volume fraction and/or reduced frequency is provided to the processing unit 21. The improved mass flow rate is determined using analytically derived or empirically derived mass flow calibration models (or formulas derived therefore), which is a function of the measured phase difference ($\Delta\phi$) and at least one of the determined GVF, reduced frequency and speed of sound, or any combination thereof, which will be described in greater detail hereinafter. For determining an improved density for the coriolis meter, the calculated gas volume fraction and/or reduced frequency is provided to the processing unit 21. The improved density is determined using analytically derived or empirically derived density calibration/parameter models (or formulas derived therefore), which is a function of the measured natural frequency and at least one of the determined GVF, reduced frequency and speed of sound, or any combination thereof, which will be described in greater detail hereinafter. The improved mass flow measurement is the mass flow rate of the aerated flow passing through the pipe.

While the improved mass flow and improved density measurement may be a function GVF, SOS and reduced frequency, the present invention contemplates these improved measurements may be a function of other parameters, such a gas damping $\zeta_{gas}$.

Further, while the functional block diagram illustrates that the processing unit 21 may improve both the density measurement and the density measurement of the coriolis meter 16, the invention contemplates that the processing may only compensate or improve one the density and mass flow rate parameters.

Figure 10:
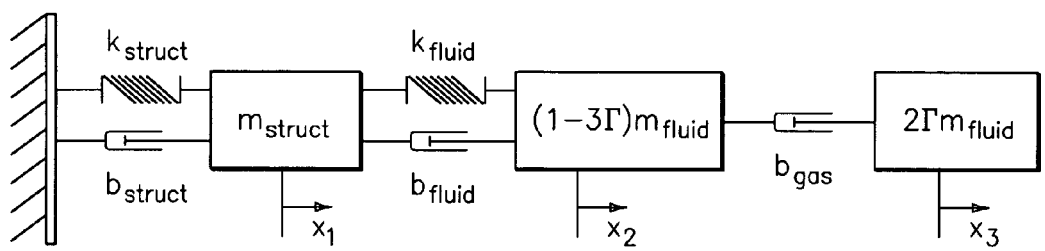
FIG. 10 is a schematic illustration of model of a coriolis meter having aerated fluid flowing therethrough that accounts for compressibility inhomogeniety of the aerated fluid, in accordance with the present invention.

Results for a lumped parameter model of FIG. 10 presented hereinafter confirm long recognized accuracy degradation of vibrating tube density meters attributed to aeration. The models can be used to illustrate qualitatively the role of several non-dimensional parameters that govern the performance of the meters in aerated fluids. It can be concluded from these models that gas volume fraction plays a dominant role, with several other parameters including gas damping $\zeta_{gas}$ and reduced frequency also influencing performance.

Although simplified models may provide some insight into the influence of various parameters, quantitative models remain elusive due to the inherent complexity of multiphase, unsteady fluid dynamics. Furthermore, the difficulty associated with correcting for the effects aeration in the interpreted density of the liquid is compounded not only by the transformation of the coriolis meter from a well understood device operating in homogeneous, quasi-steady parameter space into a device operating in a complex, non-homogeneous, unsteady operation space, but also by the inability of current coriolis meters to precisely determine the amount of aeration present in the process mixture.

The present invention provides an approach in which a speed-of-sound measurement of the process fluid is integrated with the natural frequency measurement of a vibrating tube density meter to form a system with an enhanced ability to operate accurately in aerated fluids. Introducing a real time, speed-of-sound measurement address the effects of aeration on multiple levels with the intent to enable vibrating-tube-based density measurement to continue to report liquid density in the presence of entrained air with accuracy approaching that for a non-aerated liquid. Firstly, by measuring the process sound speed with process pressure, the aeration level of the process fluid can be determined with high accuracy on a real time basis. Secondly, the real time measurements of sound speed, and the derived measurement of gas volume fraction, are then utilized with empirically derived correction factors to improve the interpretation of the measured natural frequency of the vibrating tubes in terms of the density of the aerated fluid. Thirdly, the combined knowledge of aerated mixture density and aerated mixture sound speed, enable the determination of the non-aerated liquid component density, providing improved compositional information. Note liquids phase includes pure liquids, mixtures of liquids, as well as liquid/solids mixtures.

A methodology is described to improve the accuracy of vibrating-tube-based density measurements of aerated liquids. For most density measuring devices, the presence of a small, but unknown, quantity of entrained gaseous phase within the process mixture can introduce significant errors in both the measured mixture density as well as the interpreted density of the liquid phase.

One embodiment of the present invention describes an approach to measuring fluid density which couples a sonar-based speed-of-sound measurement with vibrating-tube-based density measurement, commonly used in coriolis mass and density meters, to determine the density of aerated liquids. It is well known that the accuracy of coriolis meters can be significantly degraded with the aeration of the process fluid. Augmenting the output of the coriolis meter with a speed of sound measurement provides a novel approach to improve density measurements for aerated fluids in two ways. Firstly, sound speed based gas volume fraction measurement provides a first-principles-based, real time measurement of the gas volume fraction and compressibility of the aerated process fluid. Secondly, the sound speed of the process fluid may be used to compensate for the effect of the increased compressibility and inhomogeniety of aerated mixtures on the output of the coriolis density measurement.

To illustrate the fundamental ways in which aeration impacts vibrating-tube density measurements, a simplified, lumped parameter model for the effects of aeration in vibrating tubes is developed. The model illustrates that the effects of aeration can be attributed to at least two independent mechanisms; 1) the density inhomogeniety of discrete gas bubbles and 2) increased mixture compressibility due to aeration. Analytical results are supported by experimental data which suggest that augmenting the density measurements from the coriolis meter with a sound speed measurement significantly enhances the ability determine the density of aerated liquids with an accuracy that approaches that for non-aerated mixtures.

Coriolis Density Measurement

Although the specific design parameters of coriolis meters 16 are many and varied, all coriolis meters are essentially aeroelastic devices. Aeroelasticity is a term developed in the aeronautical sciences that describes the study of dynamic interaction of coupled fluid dynamic and structural dynamic systems, for example the static and dynamic response of an aircraft under aerodynamic forces. Coriolis flow meters rely on characterizing the aeroelastic response of fluid-filled, vibrating flow tubes 302 to determine both the mass flow rate and process fluid density measurements, see FIGS. 23 and 24.

The physical principle used to determine process fluid density in a Coriolis meter 16 is similar to that used in vibrating tube density meters. In these devices, the density of the process fluid 12 is determined by relating the natural frequency of a fluid-filled tube to the density of the process fluid. To illustrate this principle, consider the vibratory response of a vacuum-filled flow tube.

Figure 4:
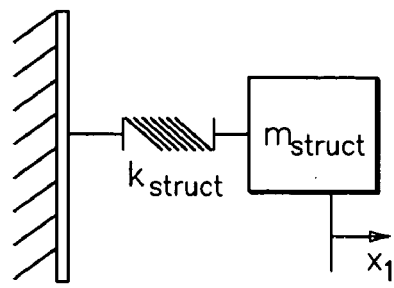
FIG. 4 is a schematic illustration of model of a coriolis meter having no fluid flowing therethrough, in accordance with the present invention.

In this model, shown schematically in FIG. 4, the frequency of oscillation is given by the ratio between the effective stiffness ($K_{struct}$) of the tubes and the effective mass ($m_{struct}$) of the tubes.

$$f_{nat} = \frac{1}{2\pi} \sqrt{\frac{K_{struct}}{m_{struct}}}$$

Figure 5:
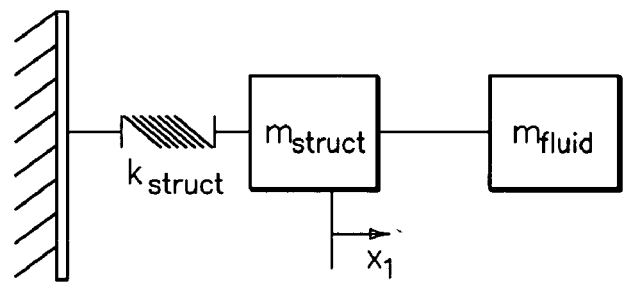
FIG. 5 is a schematic illustration of model of a coriolis meter having fluid flowing therethrough, in accordance with the present invention.

Introducing fluid to the tube changes the natural frequency of the oscillation. Under a quasi-steady and homogeneous model of the fluid 12, the primary effect of the fluid is to mass-load the tubes. The fluid typically has a negligible effect on the stiffness of the system. Thus, within the framework of this model, the mass of the fluid 12 is added directly to the mass of the structure, as shown schematically in FIG. 5.

The mass of the fluid 12 in the tube is proportional to fluid density, and therefore, the naturally frequency decreases with increasing fluid density as described below:

$$f_{nat} = \frac{1}{2\pi} \sqrt{\frac{K_{struct}}{m_{struct} + \beta \rho_{fluid}}}$$

where β is a calibrated constant related to the geometry and vibratory characteristic of the vibrating tube.

Rearranging, the algebraic relation between the measured natural frequency $f_{nat}$ of the vibrating tube and the density of the fluid within the tube can be written as follows.

$$\rho_{fluid} = \frac{1}{\beta}\left(\frac{K_{struct}}{(2\pi)^2 f_{nat}^2} - m_{struct}\right)$$

Defining the ratio between the effective mass of the fluid to that of the structure as α, the natural frequency of the fluid loaded tubes is given by:

$$f_{nat} = f_s \sqrt{\frac{1}{1+\alpha}} \text{ where } \alpha \equiv \frac{m_{fluid}}{m_{struct}}$$

This basic framework provides an accurate means to determine process fluid density under most operating conditions. However, some of the fundamental assumptions regarding the interaction of the fluid 12 and the structure can deteriorate under different operating conditions. Specifically, aerated fluids in oscillating tubes behave differently from single phase fluids in two important ways; increased compressibility, and fluid inhomogeneity.

Fluid Compressibility

It is well known that most aerated liquids are significantly more compressible than non-aerated liquids. Compressibility of a fluid is directly related to the speed of sound and density of the fluid 12.

Mixture density and sound speed can be related to component densities and sound speed through the following mixing rules which are applicable to single phase and well-dispersed mixtures and form the basis for speed-of-sound-based entrained air measurement.

$$\kappa_{mix} = \frac{1}{\rho_{mix} a_{mix_\infty}^2} = \sum_{i=1}^{N} \frac{\phi_i}{\rho_i a_i^2}$$

where $$\rho_{mix} = \sum_{i=1}^{N} \phi_i \rho_i$$

and $\kappa_{mix}$ is the mixture compressibility, and $\phi_i$ is the component volumetric phase fraction.

Consistent with the above relations, introducing air into water dramatically increases the compressibility of the mixture 12. For instance, at ambient pressure, air is approximately 25,000 times more compressible than water. Thus, adding 1% entrained air increases the compressibility of the mixture by a factor of 250. Conceptually, this increase in compressibility introduces dynamic effects that cause the dynamic of behavior of the aerated mixture within the oscillating tube to differ from that of the essentially incompressible single-phase fluid.

Figure 6:
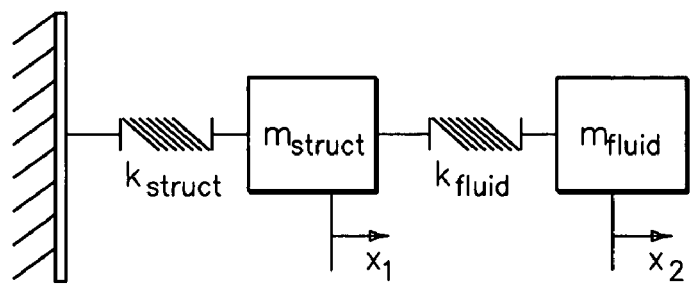
FIG. 6 is a schematic illustration of model of a coriolis meter having aerated fluid flowing therethrough that accounts for compressibility of the aerated fluid, in accordance with the present invention.

The effect of compressibility of the fluid 12 can be incorporated into a lumped parameter model of a vibrating tube as shown schematically in FIG. 6. The stiffness of the spring represents the compressibility of the fluid. As the compressibility approaches zero, the spring stiffness approaches infinity and the model becomes equivalent to that presented in FIG. 5.

As before the effective mass of the fluid 12 is proportional to the density of the fluid and the geometry of the flow tube. The natural frequency of the first transverse acoustic mode in a circular duct can be used to estimate an appropriate spring constant for the model $$f = \frac{1.84}{\pi D} a_{mix} = \frac{1}{2\pi} \sqrt{\frac{K_{fluid}}{m_{fluid}}}$$

Figure 7:
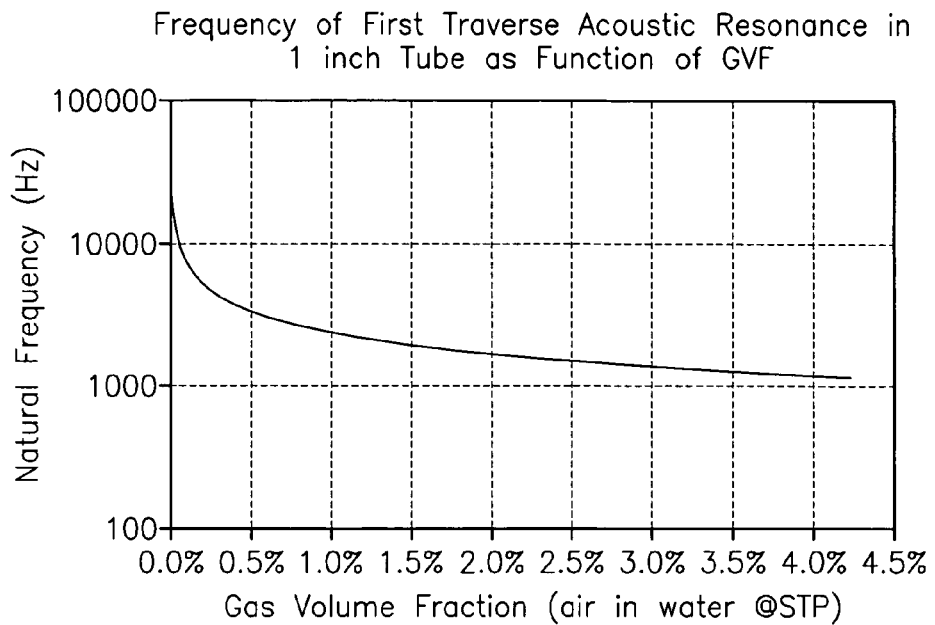
FIG. 7 is a plot of the natural frequency of the tubes as a function of the gas volume fraction of the fluid flow, in accordance with the present invention.

Note that this frequency corresponds to a wavelength of an acoustic oscillation of approximately two diameters, i.e., this transverse mode is closely related to a "half wavelength" acoustic resonance of the tube. FIG. 7 shows the resonant frequency of the first transverse acoustic mode of a one-inch tube as a function of gas volume fraction for air entrained in water at standard temperature and pressure. For low levels of entrained air, the frequency of the first transverse acoustic mode is quite high compared to the typical structural resonant frequencies of coriolis meters of 100 Hz; however, the resonant acoustic frequency decreases rapidly with increased levels of entrained air.

Figure 8:
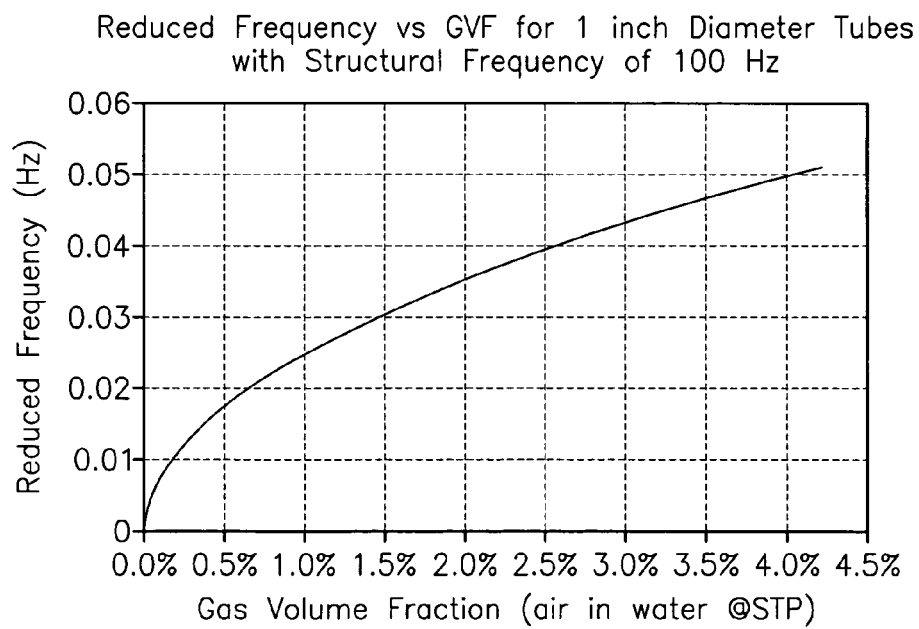
FIG. 8 is a plot of the reduced frequency as a function of the gas volume fraction of the fluid flow, in accordance with the present invention.

In characterizing aeroelastic systems, it is often convenient to define a reduced frequency parameter to gauge the significance of the interaction between coupled dynamic systems. For a vibrating tube filled with fluid, a reduced frequency can be defined as a ratio of the natural frequency of the structural system to that of the fluid dynamic system.

$$f_{red} = \frac{f_{struct} D}{a_{mix}}$$

Where $f_{struct}$ is the natural frequency of the tubes in vacuum, D is the diameter of the tubes, and $a_{mix}$ is the sound speed of the process fluid. For this application, as the reduced frequency becomes negligible compared to 1, the system approaches quasi-steady operation. In these cases, models, which neglect the compressibility of the fluid, such as that shown in FIG. 6, are likely to be suitable. However, the effects of unsteadiness increase with increasing reduced frequency. For a given coriolis meter, mixture sound speed has the dominant influence of changes in reduced frequency. FIG. 8 shows the reduced frequency plotted as a function of entrained air for a one-inch diameter tube with a structural natural frequency of 100 Hz. As shown, the reduced frequency is quite small for the non-aerated water; however, builds rapidly with increasing gas volume fraction, indicating that the significance of compressibility increases with gas volume fraction. However, when considering coriolis meters of varying design parameters, increases in tube natural frequency or tube diameter will increase the effects of unsteadiness for a given level of aeration.

Fluid Inhomogeneity

In additional to dramatically increasing the compressibility of the fluid 12, aeration introduces inhomogeneity to the fluid. For flow regimes in which the gas is entrained in a liquid-continuous flow field, the first-order effects of the aeration can be modeled using bubble theory. By considering the motion of an incompressible sphere of density of $\rho_0$ contained in an inviscid, incompressible fluid with a density of $\rho$ and set into motion by the fluid show that the velocity of the sphere is given by:

$$V_{sphere} = \frac{3\rho}{\rho + 2\rho_0} V_{fluid}$$

For most entrained gases in liquids, the density of the sphere is orders of magnitude below that of the liquid and the velocity of bubble approaches three times that of the fluid.

Considering this result in the context of the motion of a sphere in a cross section of a vibrating tube, the increased motion of the sphere compared to the remaining fluid must result in a portion of the remaining fluid having a reduced level of participation in oscillation, resulting in a reduced, apparent system inertia.

Figure 9:
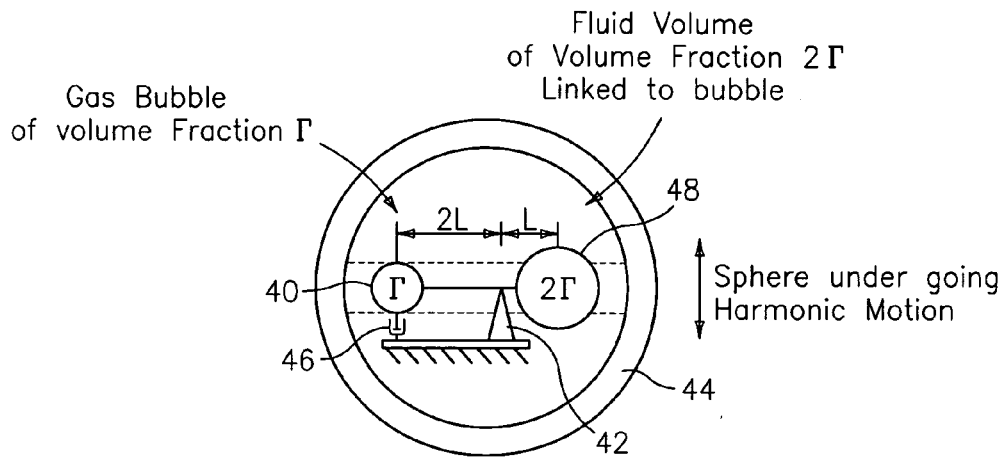
FIG. 9 is a schematic diagram of effect of fluid flow inhomogeneity with the tube of a coriolis meter, in accordance with the present invention.

FIG. 9 illustrates a lumped parameter model for the effects of inhomogeniety in the oscillation of an aerated-liquid-filled tube. In this model, a gas bubble 40 of volume fraction φ is connected across a fulcrum 42 to a compensating mass of fluid with volume 2Γ. The fulcrum is rigidly connected to the outer tube 44. The effects of viscosity can be modeled using a damper 46 connected to restrict the motion of the gas bubble 40 with respect to the rest of the liquid and the tube itself. The remaining volume of liquid in the tube cross section (1–3Γ) is filled with an inviscid fluid. In the inviscid limit, the compensating mass of fluid 48 (2Γ) does not participate in the oscillations, and the velocity of the massless gas bubble becomes three times the velocity of the tube. The effect of this relative motion is to reduce the effective inertia of the fluid inside the tube to (1−3Γ) times that presented by a homogeneous fluid-filled the tube. In the limit of high viscosity, the increased damping constant minimizes the relative motion between the gas bubble and the liquid, and the effective inertia of the aerated fluid approaches 1-Γ. The effective inertia predicted by this model of an aerated, but incompressible, fluid oscillating within a tube agrees with those presented by (Hemp, et al, 2003) in the limits of high and low viscosities.

One should appreciate that the processing unit may use these models independently or together in a lumped parameter model.

Combined Lumped Parameter Model

Models were presented with the effects of aeration on vibrating tube density meters in which the effects of compressibility and inhomogeniety were addressed independently. FIG. 10 shows a schematic of a lumped parameter model that incorporates the effects of compressibility and inhomogeniety using the mechanism-specific models developed above.

The equations of motion of the above lumped parameter model, assuming solutions in the form of $e^{s\tau}$ where s is the complex frequency, can be expressed in non-dimensional form as:

$$\begin{bmatrix} s+2\alpha\zeta_f Q+2\zeta_s & 1+\alpha Q^2 & -2\alpha\zeta_f Q & -\alpha Q^2 & 0 & 0 \\ -1 & s & 0 & 0 & 0 & 0 \\ 2\zeta_f Q & -Q^2 & (1-3\Gamma)s+2\zeta_f Q+2\zeta_g & Q^2 & -2\zeta_g & 0 \\ 0 & 0 & -1 & s & 0 & 0 \\ 0 & 0 & -2\zeta_g & 0 & 2\Gamma s+2\zeta_g & 0 \\ 0 & 0 & 0 & 0 & -1 & s \end{bmatrix} \begin{Bmatrix} y_1 \\ x_1 \\ y_2 \\ x_2 \\ y_3 \\ x_3 \end{Bmatrix} = 0$$

The parameters governing the dynamic response of the model are defined in the following Table 1.

TABLE 1

Definition of Non-dimensional Parameters Governing the Equation of Motion for the Lumped Parameter Model of a Tube Filled with a Compressible, Aerated Fluid

| Symbol | Description | Definition |
|---|---|---|
| α | Mass ratio | $m_{fluid}/m_{struct}$ |
| Q | Natural Frequency Ratio | $\omega_{fluid}/\omega_{struct}$ |
| $\zeta_f$ | Critical Damping Ratio of Fluid System | $b_{fluid}/(2m_{fluid}\omega_{fluid})$ |
| $\zeta_s$ | Critical Damping Ratio of Structural System | $b_{struc}/(2m_{struct}\omega_{sstruc})$ |
| $\zeta_g$ | Critical Damping Ratio of Structural System | $b_{gas}/(2m_{fluid}\omega_{struct})$ |
| τ | Non-dimensional time | $t\,\omega_{struct}$ |
| γ | Non-dimensional temporal derivative of x | $dx/d\tau$ |

Solving the sixth-order eigenvalue problem described above provides a means to assess the influence of the various parameters on the observed density. The natural frequency of the primary tube mode predicted by the eigenvalue analysis is input into the frequency/density from the quasi-steady, homogeneous model to determine the apparent density of the fluid 12 as follows.

$$\rho_{apparent} = \frac{\rho_{liq}}{\alpha}\left(\frac{f_s^2}{f_{observed}^2}-1\right)$$

As a baseline condition, a "representative" coriolis meter with parameters given in Table 2 was analyzed.

TABLE 2

Parameters Defining the Baseline Vibrating Tube Density Meter

| Parameter | Description | Value |
|---|---|---|
| $f_s$ | Structural Frequency of Tubes | 100 Hz |
| α | Mass ratio | 1.25 |
| $\zeta_{struct}$ | Critical Damping Ratio - structure | 0.01 |
| $\zeta_{fluid}$ | Critical Damping Ratio - fluid | 0.01 |
| $\zeta_{gas}$ | Critical Damping Ratio - gas | 0.01 |
| Q | Frequency Ratio | As determined by sound speed of air/water at STP and structural parameters |
| D | Tube diameter | 1.0 inches |

Figure 11:
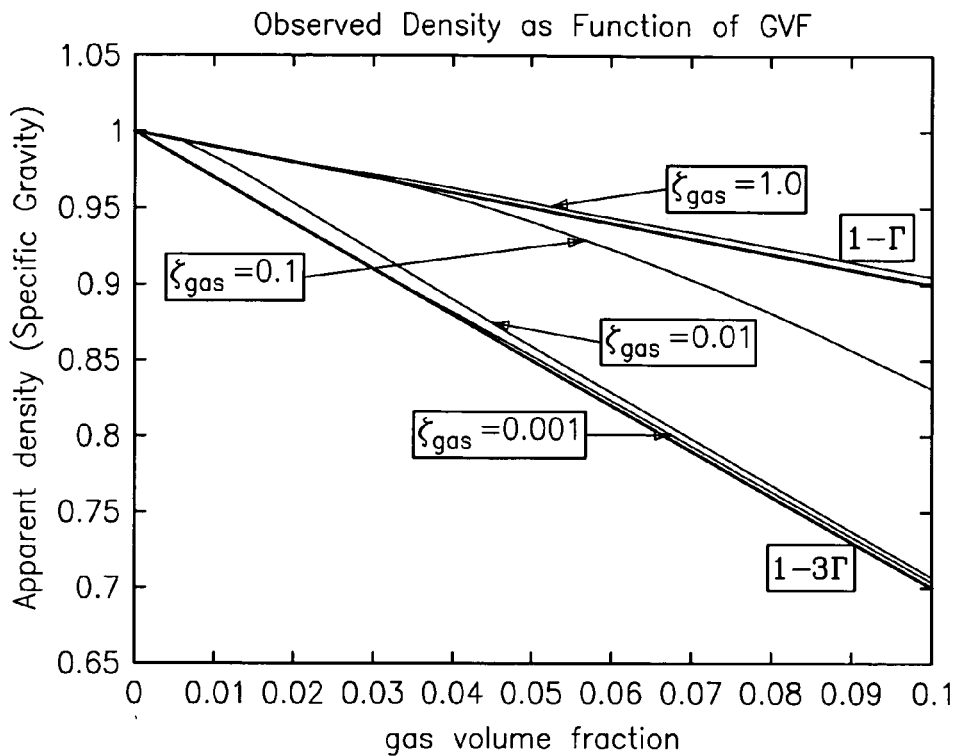
FIG. 11 is a plot of the apparent density as a function of the gas volume fraction of the fluid flow at differing critical damping rations of gas, in accordance with the present invention.

For a given coriolis meter, the level of aeration has a dominant effect on the difference between actual and apparent mixture density. However, other parameters identified by the lumped parameter model also play important roles. For example, the damping parameter associated with the movement of the gas bubble relative to the fluid within the tube, $\zeta_{gas}$, is a parameter governing the response of the system to aeration. The influence of $\zeta_{gas}$ on the apparent density of the mixture is illustrated in FIG. 11. As shown, for $\zeta_{gas}$ approaching zero, the apparent density approaches 1−3Γ, i.e., the meter under reports the density of the aerated mixture by 2Γ. However, as the $\zeta_{gas}$ is increased, the apparent density approaches the actual fluid density of 1-Γ.

Figure 12:
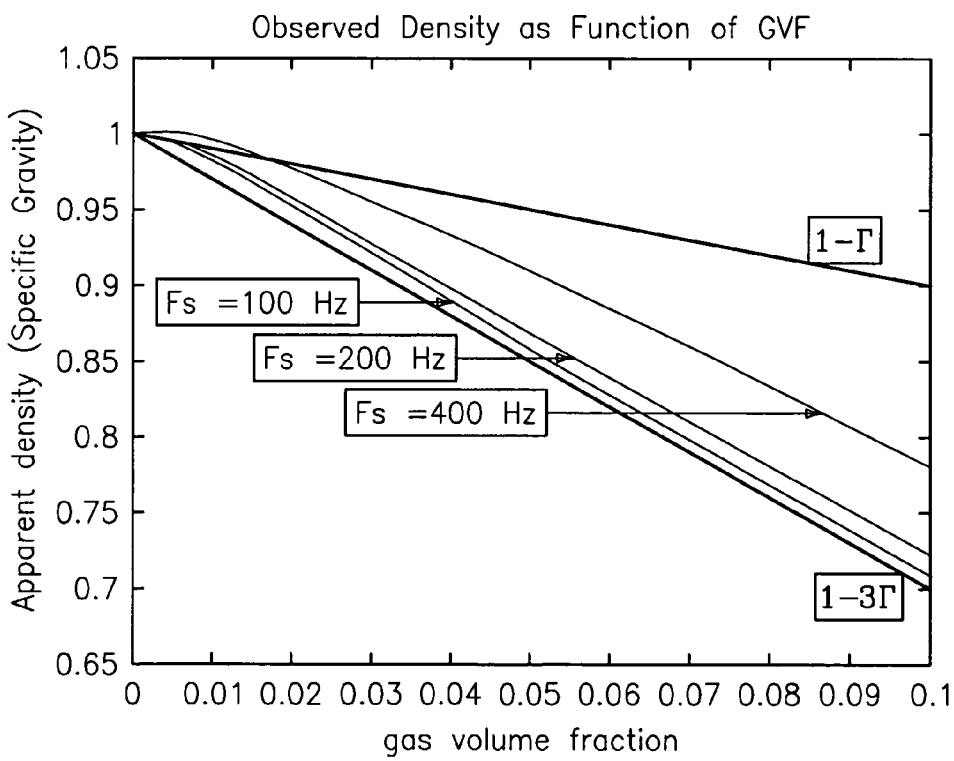
FIG. 12 is a plot of the reduced frequency as a function of the gas volume fraction of the fluid flow for a number of coriolis meters differing in the natural frequency of the tubes, in accordance with the present invention.

The influence of compressibility is illustrated in FIG. 12, in which the model-predicted observed density is shown as function of gas volume fraction for a range of meters differing only in natural frequency of the tubes. As shown, the natural frequency of the tubes, primarily through the influence of the reduced frequency of operation at a given level of aeration can significantly influence the relation between the actual and apparent density of an aerated fluid.

Experimental Data

Figure 13:
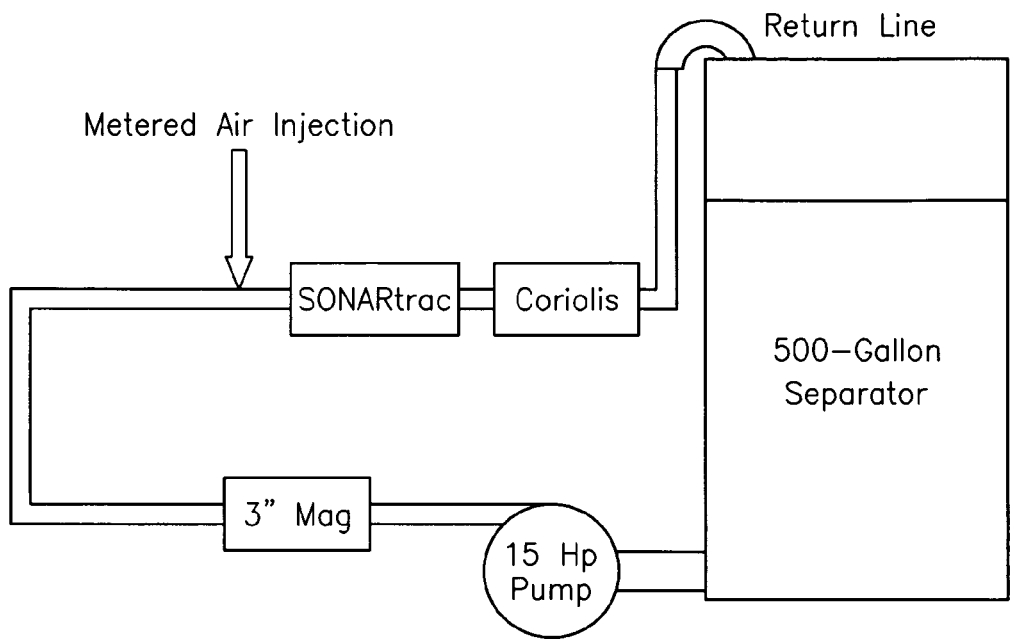
FIG. 13 is a schematic diagram of a coriolis meter/entrained air facility, in accordance with the present invention.

A facility, as shown in FIG. 13, was constructed to experimentally evaluate the performance of coriolis meters on aerated water. The facility uses a mag meter operating on single phase water as a reference flow rate and the sonar-based meter 100 to monitor the gas volume fraction of the aerated mixtures.

Figure 14:
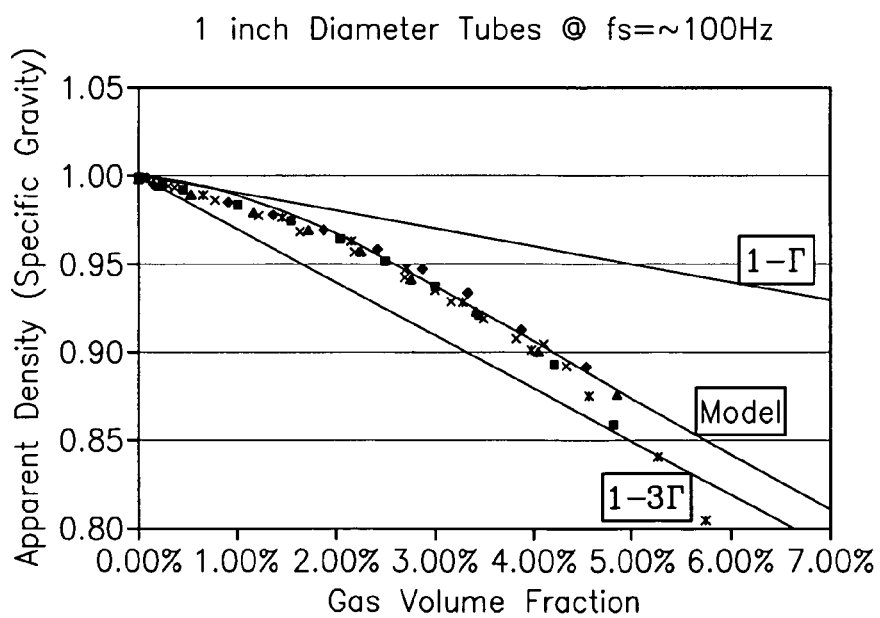
FIG. 14 is a plot of the apparent density as a function of the gas volume fraction of coriolis meter having 1 inch diameter tubes at a resonant frequency of 100 Hz, in accordance with the present invention.

The density of the liquid component of the aerated liquid, i.e. the water, was assumed constant. Several coriolis meters of various designs and manufactures were tested. FIG. 14 shows apparent density measured by a coriolis meter with 1 inch diameter tubes with a structural resonant frequency of 100 Hz. Data were recorded over flow rates ranging from 100–200 gpm and coriolis inlet pressures of 16 to 26 psi. The theoretically correct density of the aerated mixture density factor of 1-$\Gamma$ is shown, as is the result from quasi-steady inviscid bubble theory of 1–3$\Gamma$. Density factor produced by the lumped parameter with the $\zeta_{gas}$ tuned to 0.02 is also shown. As shown, the apparent density of the coriolis meter is highly correlated to the gas volume fraction as measured by the GVF meter 100. The lumped parameter model appears to capture the trend as well.

Figure 15:
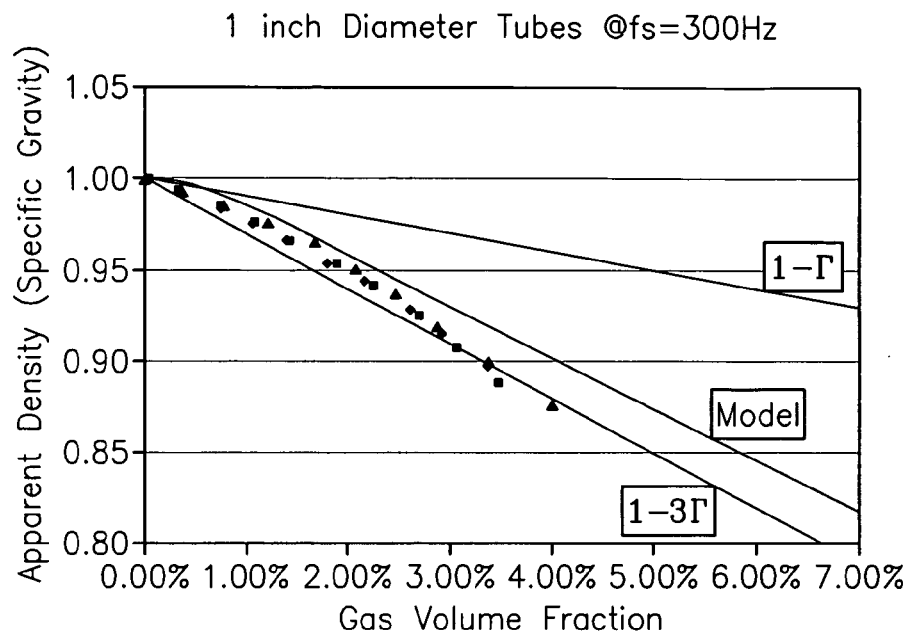
FIG. 15 is a plot of the apparent density as a function of the gas volume fraction of coriolis meter having 1 inch diameter tubes at a resonant frequency of 300 Hz, in accordance with the present invention.

FIG. 15 shows the apparent density measured by the Coriolis meter with 1 inch diameter tubes with a structural resonant frequency of ~300 Hz. Data was recorded over a similar range of flow rate and inlet pressures as the previous meter. Again, the theoretically correct density of the aerated mixture density factor of 1-$\Gamma$ is shown, as is the result from quasi-steady inviscid bubble theory of 1–3$\Gamma$. Density factor produced by the lumped parameter with the $\zeta_{gas}$ empirically tuned to 0.007 is also shown. As with the other meter tested, the apparent density of the coriolis meter 16 is highly correlated to the gas volume fraction as measured by the GVF meter 100. The correlation between the output of the lumped parameter model and the output of the density meter provides a useful framework for assessing the impact of aeration on the apparent density of the process fluid 12.

Figure 16:
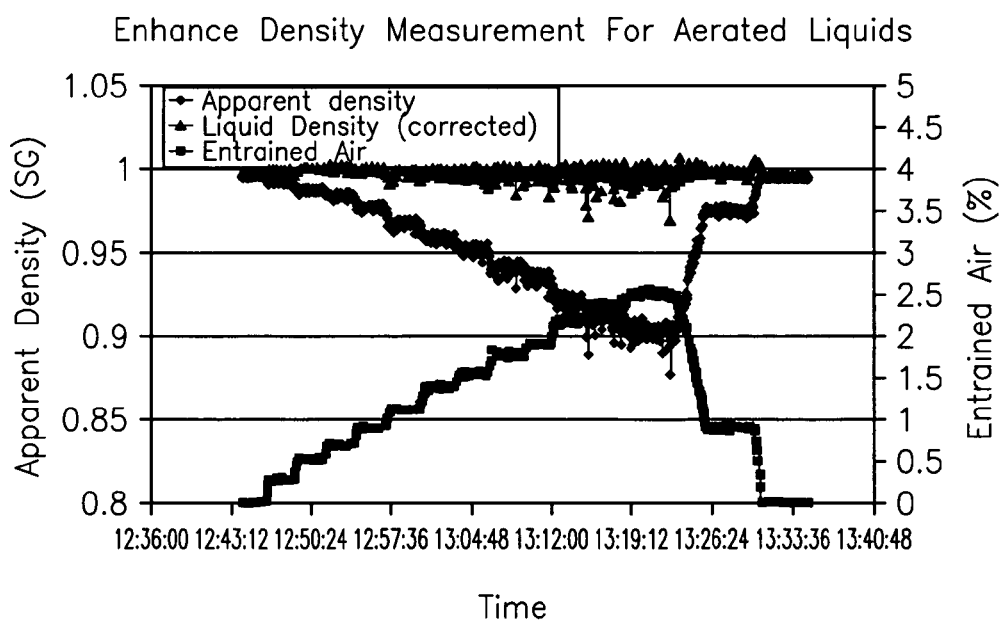
FIG. 16 is a plot of the apparent density, corrected apparent density and the gas volume fraction of coriolis meter over time as the volume of entrained air varies, in accordance with the present invention.

The performance of a speed of sound enhanced coriolis density measurement operating in the presence of entrained air is illustrated in FIG. 16. The data shows the time histories of the apparent density, entrained air, and corrected liquid density during an approximately 50 minute period over which the density meter was subjected to varying amounts of entrained air ranging from 0 to 3%. The data presented in FIG. 15 was used in conjunction with the real time entrained air measurement to quantify the difference between the actual liquid density and the apparent liquid density during the transient. As shown, the accuracy of the liquid density reported by the speed-of-sound enhanced meter is significantly improved over the apparent density output by the baseline meter.

Experimental data and analytical results demonstrate the significant impact that entrained gases have on the accuracy of vibrating tube based density measurement. Analytical models were presented illustrating the how the effects of increased fluid compressibility and inhomogeneity can introduce significant error in the interpreted density of the process fluid. Analytical models illustrated how the impact of aeration is linked to the gas volume fraction of the process fluid, the reduced frequency of the vibrating tubes, and other parameters. While analytical models have been illustrated, the present invention contemplates that empirical models may be used to compensate or improve the density and/or mass flow rate of a coriolis meter 16.

Experimental data was presented demonstrating how the advantages associated with combining a real time measurement of gas volume fraction and reduced frequency with a vibrating tube based density meter 16 can significantly improve the accuracy of both the aerated mixture density measurement as well as the measurement of the non-aerated liquid portion of the mixture.

Mass Flow Correction

The current state-of-the-art appears to utilize quasi-steady models, and empirical correlations based on quasi-steady models, to relate the measured quantities to the derived fluid parameters. This quasi-steady model for the fluid structure interactions appears to work adequately for most Coriolis meters operating with most industrial process flows. The validity of the quasi-steady assumption will scale with the reduced frequencies of the vibration of the fluid within the pipe. Under a quasi-steady framework, the higher the reduced frequencies, the less accurate the Coriolis meters become.

One relevant reduced frequency for the unsteady effects within a Corilois meter is the reduced frequency based on the vibrational frequency, tube diameter, and process fluid sound speed:

$$\tilde{f}_D = \frac{fD}{a_{mix}}$$

Another relevant reduced frequency is the that based on the overall length of the corilois tubes:

$$\tilde{f}_L = \frac{fL}{a_{mix}}$$

It should be noted that, for any given meter design in which the geometry is fixed, the two reduced frequencies are not independent, and are scalar multiples of each other. For a given meter, variations in the reduced frequencies above are primarily determined by variations in process fluid sound speed.

Physically, the reduced frequency represents the ratio between the time required for sound to propagate over a characteristic length to the time required for the tube to vibrate one cycle. From a performance and accuracy perspective, reduced frequencies serve to capture the importance of unsteadiness in the aeroelastic interaction of the fluid and structure.

In the limit of reduced frequencies approaching zero, the process can be modelled as quasi-steady. Most analytical models of Corilois flow meters use a quasi-steady model for the fluid/structure interaction. However, for non-zero reduced frequencies, unsteady effects begin to influence the relationship between the measured structural response, i.e. the phase lag in the two legs of the meters and the natural frequency, and the sought fluid parameters, i.e. the mass flow of the fluid and fluid density.

However, what is disclosed herein is to use a sound-speed based gas volume fraction parameter, a reduced frequency parameter relating to phase lag to mass flow rate.

If the reduced frequency based on diameter is non-negligible, the inertial load from the fluid on the pipe develops a slight phase lags that increases with increasing frequency. For non-negligible reduced frequencies based on the length of the flow tube, oscillations in the flow velocity can vary over the length of the pipe, potentially introducing error in the output of the meter.

Figure 17:
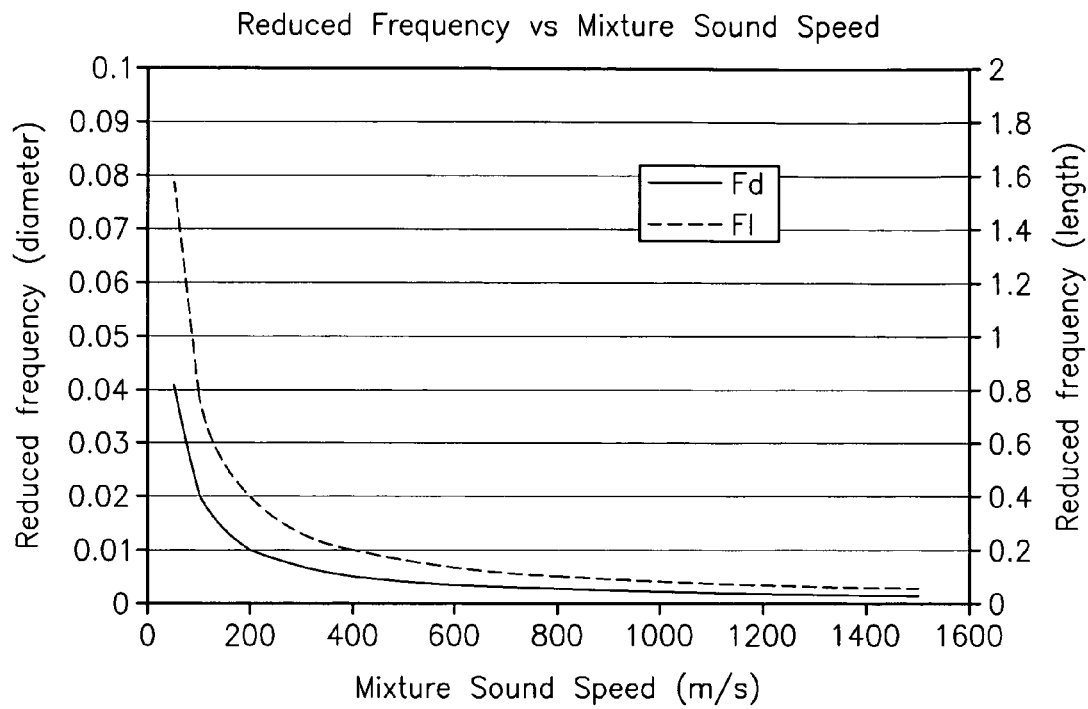
FIG. 17 is a plot of the reduced frequency as a function of the speed of sound, in accordance with the present invention.

From a dimensional perspective, a 1 inch diameter Coriolis flow tube driven at roughly 80 hz, at a maximum amplitude of 1.5 mm. For the purposes of illustrating, the length of the flow tube is estimated to be ~1 m. Using these numbers, the reduced frequency based on diameter and length are shown in FIG. 17 for mixture sound speed ranging from 1500 m/s (typical of process liquids) and 50 m/s (possible for bubbly mixtures).

As shown, typical variations in mixture sound speeds due to two phase flow result in significant variations in reduced frequencies.

Thus, by dramatically reducing mixture speed of sound, the introduction of gas to a liquid mixture can dramatically increase the reduced frequency of the primary vibration associated with the Coriolis meter. If not accounted for in the interpretation, this increase in reduced frequency renders the quasi-steady model increasing inaccurate, and results in errors in mass flow and in density.

This decrease in accuracy of Corilois meters with the introduction of bubbly fluids is well documented. In fact, others have attempted to correct for the effect of entrained air by correlating observed errors in mass flow to the gas volume fraction within the process fluid. These authors proposed a correction based on GVF as follows:

$$R = \frac{2\alpha}{1-\alpha}$$

Where the α represents the gas volume fraction and R represents decrease in measured (apparent) mass flow normalized by the true mass flow. Thus, using this correlation, a 1% increase in entrained air would result in a roughly 2% underestimate of the actual mass flow.

Although this formulation appears to capture the general trend observed experimentally, it has two drawbacks for use in the field. Firstly, the coriolis meter 16 has no direct way to measure the gas volume fraction. It has been suggested to use the measured apparent density of the fluid to estimate the level of entrained air, however, this is problematic since both of the two fundamental measurements, phase difference and natural frequency, are impacted by changes in the reduced frequency of the Coriolis vibration. Secondly, it is unlikely that the gas volume fraction is the only variable influencing the relationship between measured phase difference and mass flow and the measured natural frequency and density. Although gas volume fraction appears to correlate over at least some range of parameters, the physics of the problem suggest that sound speed, via a reduced frequency effect, mayl have also direct influence on the interpretation as developed above.

What is proposed in this disclosure is to use a direct sound measurement from the process fluid to aid in the interpretation of the coriolis meter 16. In this interpretation, the reduced frequency parameters developed herein is included in interpreting the relation between the phase difference in the vibrating tubes and the mass flow as well as a direct role in interpreting the natural frequency of the oscillating flow tubes in terms of process fluid density. The sound speed measurement, combined with knowledge of process liquid and gas components as well as process temperature and pressure, enables a direct measurement of entrained air as well. Thus, the reduced frequency parameter and gas volume fraction can be used as inputs in the interpretation of phase lag in terms of mass flow.

Due to the strong relationship between air content in liquids and mixture sound speed, the role of the reduced frequency parameter in the interpretation of the fundamental measurement of the Coriolis meter will have a more pronounce effect in bubbly flows. However, changes in sound speed and hence reduced frequency of operation in various types of liquids and other process mixtures have an effect on the interpretation and hence accuracy of Coriolis meter used in these applications as well. Consider, flow example, the performance of a Coriolis meter on two liquids—water and oil. Assume that the fluids have different densities and sound speeds. The different fluid properties suggest that the Coriolis meters will be operating at different reduced frequencies. The reduced frequency for the water will typically be ~10%–30% lower than that for the oil application.

Recognizing that, while they are different, the reduced frequencies for both applications are still "small", the impact on accuracy may not be significant. However, some degree of inaccuracy is introduced by not accounting for the differences in the reduced frequency of operation of the Coriolis meter in this application.

The basic concept disclosed herein was demonstrated in a water and air loop at near ambient pressures and temperature. The experimental set-up is shown in FIG. 13.

Figure 18:
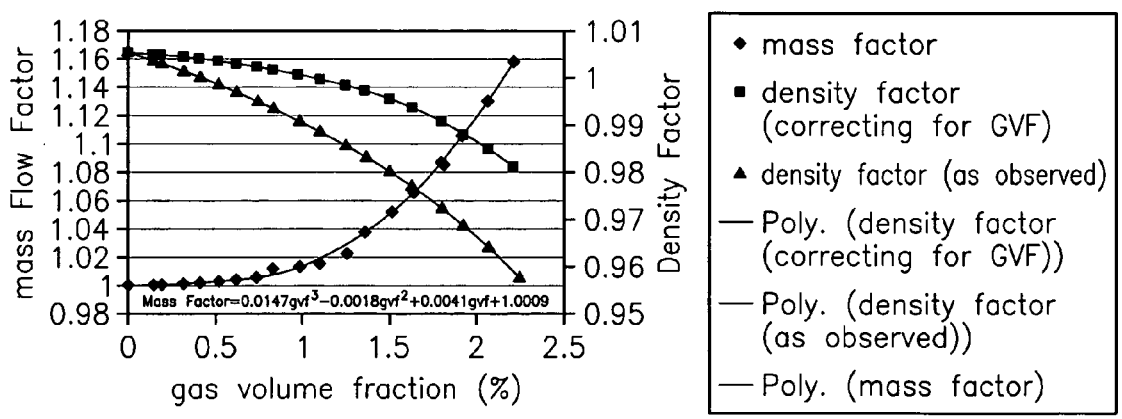
FIG. 18 is a plot of the density factor and mass flow factor as a function of the gas volume fraction, in accordance with the present invention.

In this facility, water is pumped from the bottom of a large separator through a mag meter which measures the volumetric flow rate of the water. The water then flows through a SONARtrac entrained air meter to verify that the water has negligible entrained air. Air is then injected into the water forming a two phase mixture. The amount of entrained air is then measured with a second SONARtrac meter. The two phase mixture, of known water and air composition then passes through a 3 inch, bent tube Corilois meter. The output s of all of the above mentioned metering devices where recorded along with water pressure and temperature. Using this information, the errors associated with the coriolis meter operating in the aerated liquids can be determined and plotted as a function of sound speed based parameters. In this example, Coriolis meter performance is characterized as a function of gas volume fraction. Errors in mass flow, mixture density, and observed mixture density are shown in FIG. 18.

As shown, the errors are indeed significant. At 2% entrained air, the Coriolis meter is over reporting mass flow by 15% and under reporting mixture density by 2%. The actual density being reported by the meter, if interpreted as the density of the liquid phase in the meter would be roughly 4% in error.

For this example, the mass flow error is parameterized by the sound speed-based gas volume fraction of entrained air. The parametric dependence of this is given by the equation shown on the plot.

Mass Factor=0.0147 $gvf^3$−0.0018$gvf^2$+0.0041$gvf$+ 1.0009

Figure 19:
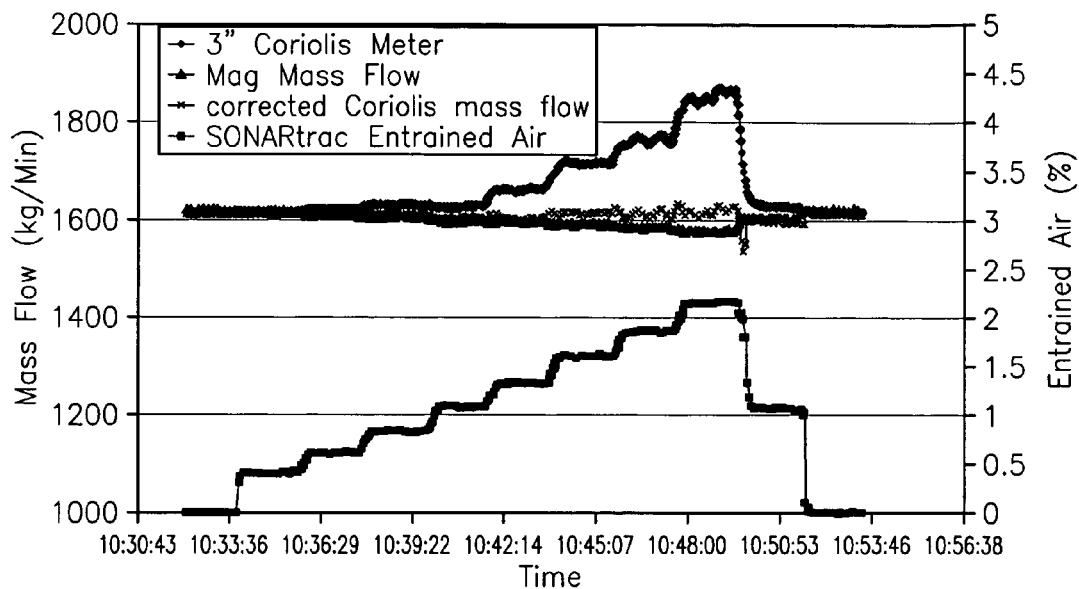
FIG. 19 is a plot of the mass flow rate, corrected mass flow rate and the gas volume fraction of a coriolis meter and the mass flow rate measured by a mag meter over time as the volume of entrained air varies, in accordance with the present invention.

This correlation was then used to correct for the coriolis mass flow for the presence of entrained air. FIG. 19 shows a time series of data in which the amount of entrained air injected upstream of the Coriolis meter was varied in small increments such that the total entrained air levels ranged from 0 to 2%. As shown, the Coriolis meter registers and significant errors in mass flow (up to 15%) due to entrained air an the gas volume fraction based correlation employed successfully corrects the mass flow errors to within roughly 1% for the demonstration.

FIG. 20 illustrates a gas volume fraction meter 100 of FIG. 2, as described herein before. The GVF meter 100 includes a sensing device 116 disposed on the pipe 14 and a processing unit 124. The sensing device 116 comprises an array of strain-based sensors or pressure sensors 118–121 for measuring the unsteady pressures produced by acoustic waves propagating through the flow 12 to determine the speed of sound (SOS). The pressure signals $P_1(t)$–$P_N(t)$ are provided to the processing unit 124, which digitizes the pressure signals and computes the SOS and GVF parameters. A cable 113 electronically connects the sensing device 116 to the processing unit 124. The analog pressure sensor signals $P_1(t)$–$P_N(t)$ are typically 4–20 mA current loop signals.

The array of pressure sensors 118–121 comprises an array of at least two pressure sensors 118,119 spaced axially along the outer surface 122 of the pipe 14, having a process flow 112 propagating therein. The pressure sensors 118–121 may be clamped onto or generally removably mounted to the pipe by any releasable fastener, such as bolts, screws and clamps. Alternatively, the sensors may be permanently attached to, ported in or integral (e.g., embedded) with the pipe 14. The array of sensors of the sensing device 116 may include any number of pressure sensors 118–121 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desire update rate of the output parameter provided by the apparatus 100. The pressure sensors 118–119 measure the unsteady pressures produced by acoustic waves propagating through the flow, which are indicative of the SOS propagating through the fluid flow 12 in the pipe. The output signals ($P_1(t)$–$P_N(t)$) of the pressure sensors 118–121 are provided to a pre-amplifier unit 139 that amplifies the signals generated by the pressure sensors 118–121. The processing unit 124 processes the pressure measurement data $P_1(t)$–$P_N(t)$ and determines the desired parameters and characteristics of the flow 12, as described hereinbefore.

The apparatus 100 also contemplates providing one or more acoustic sources 127 to enable the measurement of the speed of sound propagating through the flow for instances of acoustically quiet flow. The acoustic source may be a device the taps or vibrates on the wall of the pipe, for example. The acoustic sources may be disposed at the input end of output end of the array of sensors 118–121, or at both ends as shown. One should appreciate that in most instances the acoustics sources are not necessary and the apparatus passively detects the acoustic ridge provided in the flow 12, as will be described in greater detail hereinafter. The passive noise includes noise generated by pumps, valves, motors, and the turbulent mixture itself.

As suggested and further described in greater detail hereinafter, the apparatus 10 has the ability to measure the speed of sound (SOS) by measuring unsteady pressures created by acoustical disturbances propagating through the flow 12. Knowing or estimating the pressure and/or temperature of the flow and the speed of sound of the acoustic disturbances or waves, the processing unit 124 can determine gas volume fraction, such as that described in U.S. patent application Ser. No. 10/349,716, filed Jan. 23, 2003, U.S. patent application Ser. No. 10/376,427, filed Feb. 26, 2003, U.S. patent application Ser. No. 10/762,410, filed Jan. 21, 2004, which are all incorporated by reference.

Similar to the apparatus 100 of FIG. 20, an apparatus 200 of FIG. 21 embodying the present invention has an array of at least two pressure sensors 118,119, located at two locations $x_1,x_2$ axially along the pipe 14 for sensing respective stochastic signals propagating between the sensors 118,119 within the pipe at their respective locations. Each sensor 118,119 provides a signal indicating an unsteady pressure at the location of each sensor, at each instant in a series of sampling instants. One will appreciate that the sensor array may include more than two pressure sensors as depicted by pressure sensor 120,121 at location $x_3,x_N$. The pressure generated by the acoustic pressure disturbances may be measured through strained-based sensors and/or pressure sensors 118–121. The pressure sensors 118–121 provide analog pressure time-varying signals $P_1(t),P_2(t),P_3(t),P_N(t)$ to the signal processing unit 124. The processing unit 124 processes the pressure signals to first provide output signals 151,155 indicative of the speed of sound propagating through the flow 12, and subsequently, provide a GVF measurement in response to pressure disturbances generated by acoustic waves propagating through the flow 12.

The processing unit 124 receives the pressure signals from the array of sensors 118–121. A data acquisition unit 154 digitizes pressure signals $P_1(t)$–$P_N(t)$ associated with the acoustic waves 14 propagating through the pipe 114. An FFT logic 156 calculates the Fourier transform of the digitized time-based input signals $P_1(t)$–$P_N(t)$ and provide complex frequency domain (or frequency based) signals $P_1(\omega),P_2(\omega),P_3(\omega),P_N(\omega)$ indicative of the frequency content of the input signals.

A data accumulator 158 accumulates the additional signals $P_1(t)$–$P_N(t)$ from the sensors, and provides the data accumulated over a sampling interval to an array processor 160, which performs a spatial-temporal (two-dimensional) transform of the sensor data, from the xt domain to the k-ω domain, and then calculates the power in the k-ω plane, as represented by a k-ω plot, similar to that provided by the convective array processor 146.

To calculate the power in the k-ω plane, as represented by a k-ω plot (see FIG. 22) of either the signals or the differenced signals, the array processor 160 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 118–121.

Figure 22:
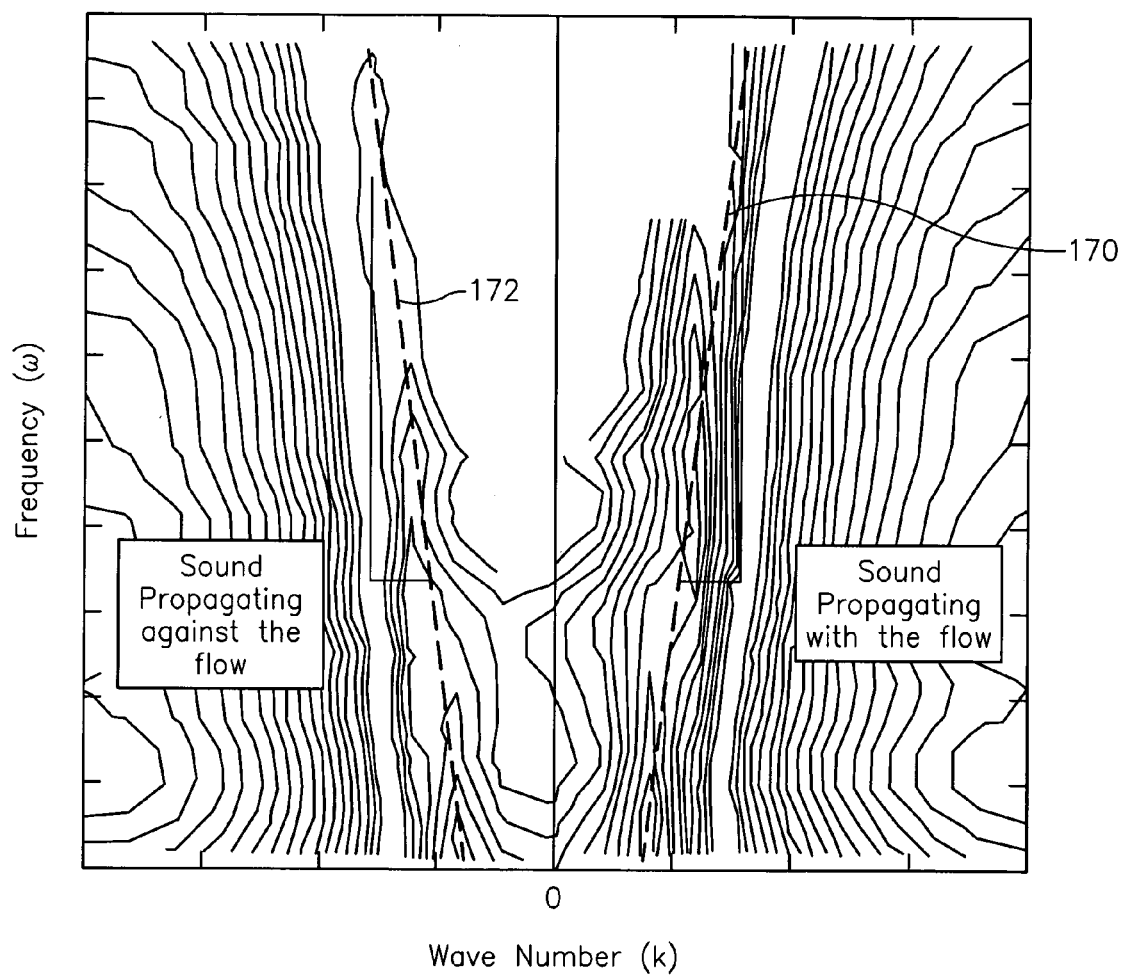
FIG. 22 is a kω plot of data processed from an array of pressure sensors use to measure the speed of sound of a fluid flow passing in a pipe, in accordance with the present invention.

In the case of suitable acoustic waves being present in both axial directions, the power in the k-ω plane shown in a k-ω plot of FIG. 22 so determined will exhibit a structure that is called an acoustic ridge 170,172 in both the left and right planes of the plot, wherein one of the acoustic ridges 170 is indicative of the speed of sound traveling in one axial direction and the other acoustic ridge 172 being indicative of the speed of sound traveling in the other axial direction. The acoustic ridges represent the concentration of a stochastic parameter that propagates through the flow and is a mathematical manifestation of the relationship between the spatial variations and temporal variations described above. Such a plot will indicate a tendency for k-ω pairs to appear more or less along a line 170,172 with some slope, the slope indicating the speed of sound.

The power in the k-ω plane so determined is then provided to an acoustic ridge identifier 162, which uses one or another feature extraction method to determine the location and orientation (slope) of any acoustic ridge present in the left and right k-ω plane. The velocity may be determined by using the slope of one of the two acoustic ridges 170,172 or averaging the slopes of the acoustic ridges 170,172.

Finally, information including the acoustic ridge orientation (slope) is used by an analyzer 164 to determine the flow parameters relating to measured speed of sound, such as the consistency or composition of the flow, the density of the flow, the average size of particles in the flow, the air/mass ratio of the flow, gas volume fraction of the flow, the speed of sound propagating through the flow, and/or the percentage of entrained air within the flow.

An array processor 160 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

One such technique of determining the speed of sound propagating through the flow 12 is using array processing techniques to define an acoustic ridge in the k-ω plane as shown in FIG. 22. The slope of the acoustic ridge is indicative of the speed of sound propagating through the flow 12. The speed of sound (SOS) is determined by applying sonar arraying processing techniques to determine the speed at which the one dimensional acoustic waves propagate past the axial array of unsteady pressure measurements distributed along the pipe 14.

The apparatus 200 of the present invention measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and flow 12 may be determined using a number of known techniques, such as those set forth in U.S. patent application Ser. No. 09/344,094, filed Jun. 25, 1999, now U.S. Pat. No. 6,354,147; U.S. patent application Ser. No. 10/795,111, filed Mar. 4, 2004; U.S. patent application Ser. No. 09/997,221, filed Nov. 28, 2001, now U.S. Pat. No. 6,587,798; U.S. patent application Ser. No. 10/007,749, filed Nov. 7, 2001, and U.S. patent application Ser. No. 10/762,410, filed Jan. 21, 2004, each of which are incorporated herein by reference.

While the sonar-based flow meter using an array of sensors 118–121 to measure the speed of sound of an acoustic wave propagating through the mixture is shown and described, one will appreciate that any means for measuring the speed of sound of the acoustic wave may used to determine the entrained gas volume fraction of the mixture/fluid or other characteristics of the flow described hereinbefore.

The analyzer 164 of the processing unit 124 provides output signals indicative of characteristics of the process flow 12 that are related to the measured speed of sound (SOS) propagating through the flow 12. For example, to determine the gas volume fraction (or phase fraction), the analyzer 164 assumes a nearly isothermal condition for the flow 12. As such the gas volume fraction or the void fraction is related to the speed of sound by the following quadratic equation:

$Ax^2+Bx+C=0$ wherein x is the speed of sound, $A=1+rg/rl*(K_{eff}/P-1)-K_{eff}/P$, $B=K_{eff}/P-2+rg/rl$; $C=1-K_{eff}/rl*a_{meas}^2$; Rg=gas density, $K_{eff}$=effective K (modulus of the liquid and pipewall), P=pressure, and $a_{meas}$=measured speed of sound.

Effectively,

Gas Voulume Fraction $(GVF)=(-B+\sqrt{B^2-4*A*C)})/(2*A)$

Alternatively, the sound speed of a mixture can be related to volumetric phase fraction ($\phi_i$) of the components and the sound speed (a) and densities ($\rho$) of the component through the Wood equation.

$$\frac{1}{\rho_{mix}a_{mix_\infty}^2} = \sum_{i=1}^{N}\frac{\phi_i}{\rho_i a_i^2} \text{ where } \rho_{mix} = \sum_{i=1}^{N}\rho_i\phi_i$$

One dimensional compression waves propagating within a flow 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{\frac{1}{a_{mix_\infty}^2} + \rho_{mix}\frac{2R}{Et}}} \qquad (\text{eq 1})$$

Figure 23:
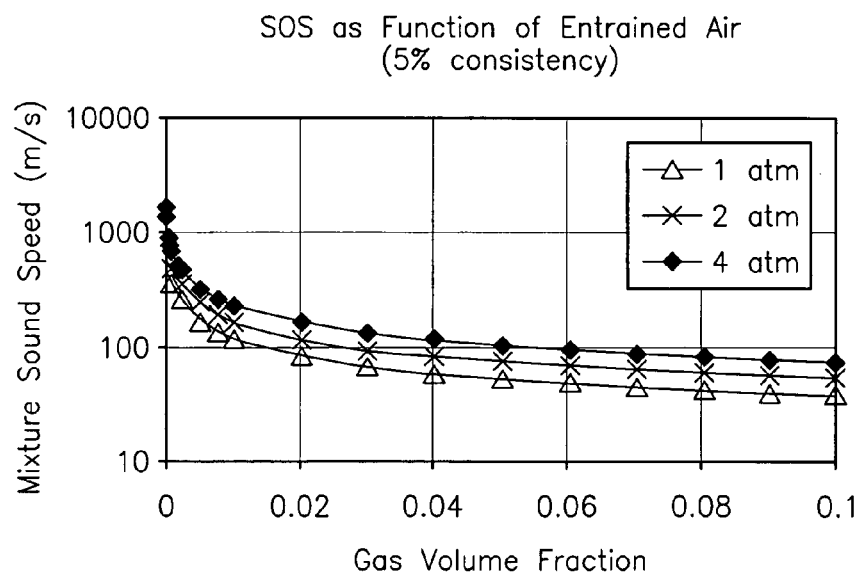
FIG. 23 is a plot of the speed of sound of the fluid flow as a function of the gas volume fraction over a range of different pressures, in accordance with the present invention.

The mixing rule essentially states that the compressibility of a mixture ($1/(\rho a^2)$) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 23.

Some or all of the functions within the processing unit 24 may be implemented in software (using a microprocessor or computer) and/or firmware, or may be implemented using analog and/or digital hardware, having sufficient memory, interfaces, and capacity to perform the functions described herein.

Figure 24:
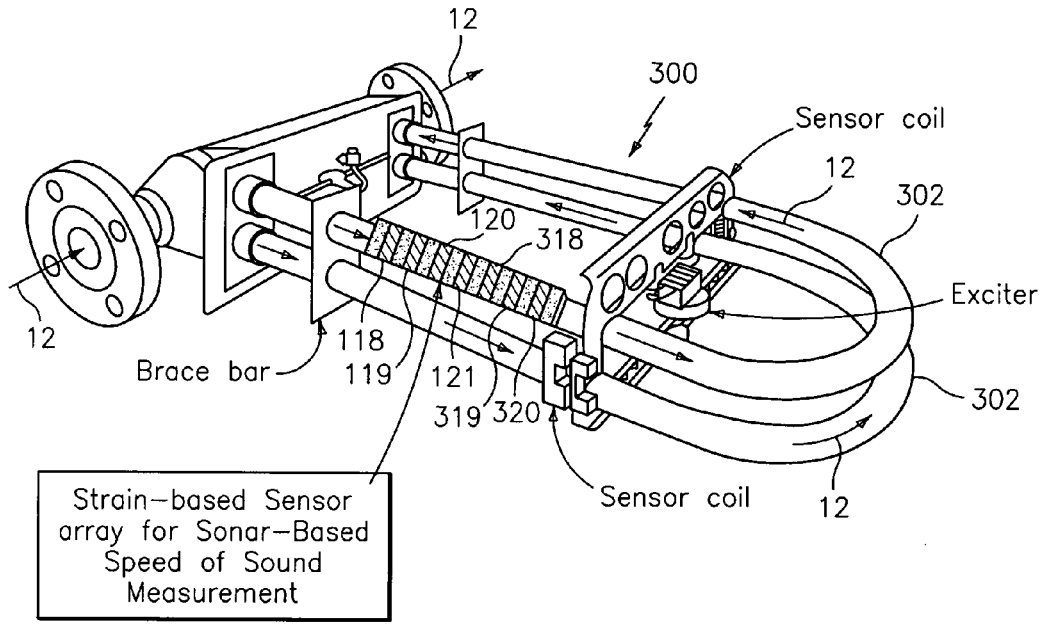
FIG. 24 is perspective view of a flow measuring apparatus including a coriolis meter having an array of sensors disposed on one of the tubes, in accordance with the present invention.
Figure 25:
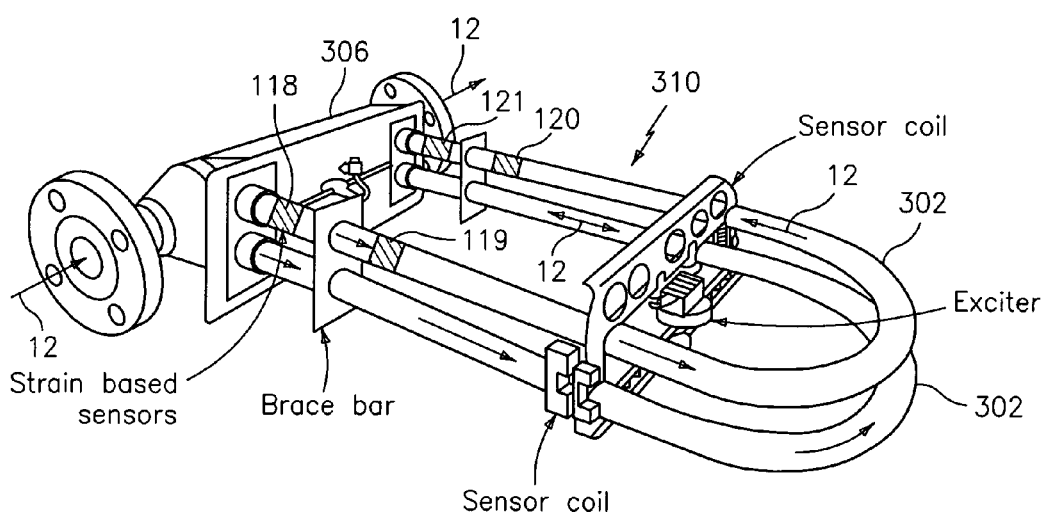
FIG. 25 is perspective view of another flow measuring apparatus including a coriolis meter having an array of sensors disposed on one of the tubes, in accordance with the present invention.

While the embodiments of the present invention shown in FIGS. 2, 20 and 21 shown the pressure sensors 118–121 disposed on the pipe 14, separate from the coriolis meter, the present invention contemplates that the GVF meter 100 may be integrated with the coriolis meter to thereby provide a single apparatus as shown in FIGS. 24 and 25. As shown in these Figures, the pressure sensors 118–121 may be disposed on one or both of the tubes 302 of the coriolis meters 300, 310.

Referring to FIG. 24, a dual tube 302 coriolis meter 300 is provided having an array of pressure sensors 118–121, 318–320 disposed on a tube 302 of the coriolis meter. In this embodiment, an array of piezoelectric material strip 50 are disposed on a web and clamped onto the tube 302 as a unitary wrap. This configuration is similar to that described in U.S. patent application Ser. No. 10/795,111, filed on Mar. 4, 2004, which is incorporated herein by reference. Similar to that described herein before, the pressure signals are provided to a processing unit to calculate at least one of the SOS, GVF and reduced frequency.

FIG. 25 illustrates another embodiment of the present invention that integrated the pressure sensors 118–121 within the coriolis meter 310. The advantages associated with integrating sonar array into the existing footprint of a Coriolis meter are numerous and include cost advantages, marketing advantages and potential for performance advantages.

The flow tubes 302 employed in Coriolis meter are many and varied. Typically the flow is diverted from the center line of the pipe to which the coriolis meter is attached, however, Coriolis meters employing straight tubes, in line with the process pipe, have also been introduced. The most common type is the U-tube coriolis meter as shown in FIG. 25. Despite the varied shapes, coriolis flow tubes are typical long and relatively slender, bent or straight. For bent tube coriolis meters, the flow tubes are typically of constant and reduced, cross-sectional than the pipe 14 to which the meter is attached, resulting in increased fluid velocity through the flow tubes. These two characteristics make the flow tubes well suited as an acoustic waveguide for low frequency acoustic waves.

Low frequency acoustic waves refer to waves for which the wavelength is significantly larger than the diameter of the flow tube 302. As we will see, for coriolis flow tubes, typically on the order of 1 inch in diameter, this definition of low frequency is not very restrictive. Thus, for a 1 inch diameter flow tube conveying water, the acoustic waves with frequencies significantly below 60,000 hz are considered low frequency (1 inch*(1 ft/12 inches)*5000 ft/sec)

For these low frequency waves, the bends in the coriolis flow tubes 302 do not have any significant effect on the propagation velocity of the acoustics. Thus, the coriolis flow tubes 302 are well suited to serve as the waveguide on which to deploy and array of sensors with which to determine the speed of sound of the mixture.

Most coriolis meters have highly tuned, well balanced sets of flow tubes. It is important to minimize any impact of the sensor on the dynamics of the flow tubes. For the U-tube shown in FIG. 25 sensors as shown deployed near the body 306 of the meter where the tubes 302 or essentially cantilevered. By attaching lightweight, strain based sensors 118–121 at this position, the dynamics of the flow tube should be essentially unaffected by the sensor array. Further, placing the two groups of sensors 118,119 and 120,121 at the ends allows the sensor array aperture to span the entire flow tube. Instrumenting the flow tubes as described herein maximize the aperture of the sensor array contained within a coriolis meter. Locating multiple sensors, but relatively closely spaced sensors near the ends results in a non-uniformly spaced array. Initial data processed with such arrays indicates that this approach will be suitable.

While integrated coriolis meters 300,310 of FIGS. 24 and 25 are U-shaped, the present invention contemplates that the sensor array may similarly disposed on a tube of a straight tube coriolis meter.

For any embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe if desired.

It is also within the scope of the present invention that any other strain sensing technique may be used to measure the variations in strain in the pipe, such as highly sensitive piezoelectric, electronic or electric, strain gages attached to or embedded in the pipe. Accelerometers may be also used to measure the unsteady pressures. Also, other pressure sensors may be used, as described in a number of the aforementioned patents, which are incorporated herein by reference.

In another embodiment, the sensor may comprise of piezofilm or strips (e.g. PVDF) as described in at least one of the aforementioned patent applications.

While the illustrations show four sensors mounted or integrated in a tube of the coriolis meter, the invention contemplates any number of sensors in the array as taught in at least one of the aforementioned patent applications. Also the invention contemplates that the array of sensors may be mounted or integrated with a tube of a coriolis meter having shape, such as pretzel shape, U-shaped (as shown), straight tube and any curved shape.

The invention further contemplated providing an elongated, non-vibrating (or oscillating) portion that permits a greater number of sensors to be used in the array.

While the present invention describes an array of sensors for measuring the speed of sound propagating through the flow for use in interpreting the relationship between coriolis forces and the mass flow through a coriolis meter. Several other methods exists.

For example, for a limited range of fluids, an ultrasonic device could be used to determine speed of sound of the fluid entering. It should be noted that the theory indicates that the interpretation of coriolis meters will be improved for all fluids if the sound speed of the process fluid is measured and used in the interpretation. Thus, knowing that the sound speed of the fluid is 5000 ft/sec as it would be for a water like substance, compared to 1500 ft/sec as it would be for say supercritical ethylene, would improve the performance of a coriolis based flow and density measurement. These measurements could be performed practically using existing ultrasonic meters.

Another approach to determine speed of sound of the fluids is to measure the resonant frequency of the acoustic modes of the flow tubes. When installed in a flow line, the cross sectional area changes associated with the transition from the pipe into the typically much smaller flow tubes creates a significant change in acoustic impedance. As a result of this change in impedance, the flow tube act as somewhat of a resonant cavity. By tracking the resonant frequency of this cavity, one could determine the speed of sound of the fluid occupying the cavity. This could be performed with a single pressure sensitive device, mounted either on the coriolis meter, of on the piping network attached to the coriolis meter.

In a more general aspect, the present invention contemplates the abllity to augmenting the performance of a coriolis meter using any method or means for measuring the gas volume fraction of the fluid flow.

In one embodiment of the present invention as shown in FIG. 20, each of the pressure sensors 118–121 may include a piezoelectric film sensor to measure the unsteady pressures of the fluid flow 12 using either technique described hereinbefore.

The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., acoustic waves) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818, U.S. patent application Ser. No. 10/712,833, and U.S. patent application Ser. No. 10/795,111, which are incorporated herein by reference.

Another embodiment of the present invention include a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 118–121, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 118–121 of FIG. 20 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 118–121 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 115–118 and it may measure the unsteady (or dynamic or ac) pressure variations inside the pipe or tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

While a number of sensor have been described, one will appreciate that any sensor the measures the speed of sound propagating through the fluid may be used with the present invention, including ultrasonic sensors.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring density of an aerated fluid flowing in a pipe; the system comprising:
   a meter having at least one vibratable tube wherein the fluid flows therethrough, the meter providing a natural frequency signal indicative of a natural frequency of the at least one vibratable tube;
   a device having at least one sensor disposed at the pipe or the at least one tube to measure the speed of sound propagating through the fluid, the device providing an SOS signal indicative of the speed of sound propagating through the fluid; and
   a processing unit to determine a density signal indicative of the density of the non-gaseous portion of the aerated fluid in response to the natural frequency signal and the SOS signal.

2. The apparatus of claim 1, wherein the SOS signal is used to determine a GVF signal indicative of a gas volumetric fraction (GVF) of the fluid.

3. The apparatus of claim 1, wherein the at least one tube of the meter is bent or straight.

4. The apparatus of claim 1 wherein the processing unit determines a composition signal indicative of the phase fraction of the fluid in response to the density signal and the SOS signal.

5. The apparatus of claim 1, wherein the device provides at least one of the SOS signal, a GVF signal indicative of the gas volume fraction of the fluid and a reduced frequency signal indicative of the reduced frequency of the fluid; and
   wherein the processing unit determines the density signal indicative of the density of the non-gaseous portion of the fluid in response to at least the natural frequency signal, and at least one of the SOS signal, the GVF signal and the reduced frequency signal.

6. The apparatus of claim 1, wherein the at least one sensor is an array of sensors having at least three sensors axially spaced along the pipe or the at least one tube.

7. The apparatus of claim 1, wherein the at least one sensor is an array of sensors having at least 4, 5, 6, 7, 8, 9, 10, 11, 12, 13, 14, 15, or 16 sensors axially spaced along the pipe or the at least one tube.

8. The apparatus of claim 1, wherein the meter is a coriolis meter.

9. The apparatus of claim 1, wherein the processing unit determines a density signal indicative of the density of the non-gaseous portion of the aerated fluid in response to the natural frequency signal, the SOS signal, and a pressure signal indicative of the pressure of the fluid.

10. The apparatus of claim 1, further includes a pressure sensor to provide a pressure signal indicative of the pressure of the fluid, and
    wherein the processing unit determines a density signal indicative of the density of the non-gaseous portion of the aerated fluid in response to the natural frequency signal, the pressure signal, and the SOS signal.

11. The apparatus of claim 1, wherein the at least one sensor includes a pressure sensor, ported pressure sensor, ultrasonic sensor, or ported ultrasonic sensor.

12. The apparatus of claim 1, wherein the natural frequency signal is used to determine the density of the aerated fluid.

13. The apparatus of claim 1, wherein the at least one sensor is an array of sensors having at least two sensors axially spaced along the pipe or the at least one tube.

14. The apparatus of claim 13, wherein the array of sensors includes strain based sensors to measure acoustic pressures in the pipe or the at least one tube.

15. The apparatus of claim 13, wherein the array of sensors are disposed on non-vibrating portions of the at least one vibratable tube.

16. The apparatus of claim 14, wherein the acoustic pressure is a one dimensional acoustic wave propagating axially through the fluid in the pipe or the at least one tube.

17. A method of measuring density of an airated fluid flowing in a pipe; the method comprising:
    providing a natural frequency signal indicative of a natural frequency of at least one vibratable tube;
    providing an SOS signal indicative of the speed of sound propagating through the fluid; and
    determining a density signal indicative of the density of the non-gaseous portion of the aerated fluid in response to the natural frequency signal and the SOS signal.

18. The method of claim 17, wherein the at least one tube of the meter is bent or straight.

19. The method of claim 17 further includes determining a composition signal indicative of the phase fraction of the fluid in response to the density signal and the SOS signal.

20. The method of claim 17, further includes providing at least one of the SOS signal, a GVF signal indicative of the gas volume fraction of the fluid and a reduced frequency signal indicative of the reduced frequency of the fluid; and
    determining the density signal indicative of the density of the non-gaseous portion of the fluid in response to at least the natural frequency signal, and at least one of the SOS signal, the GVF signal and the reduced frequency signal.

21. The method of claim 17, wherein the meter is a coriolis meter.

22. The method of claim 17, further includes determining the density of the aerated fluid in response to the natural frequency signal.

23. The method of claim 17, wherein the determining the density signal further includes determining the density signal indicative of the density of the non-gaseous portion of the aerated fluid in response to the natural frequency signal, the SOS signal, and a pressure signal indicative of the pressure of the fluid.

24. The method of claim 21, further includes measuring the pressure of a fluid.

25. The method of claim 17, further includes determining a GVF signal indicative of a gas volumetric fraction (GVF) of the fluid in response to the SOS signal.

26. The method of claim 17, wherein the providing an SOS signal includes using a at least one sensor disposed at the pipe or the at least one tube to determine the speed of sound propagating through the fluid.

27. The method of claim 26, wherein the at least one sensor is an array of sensors having at least three sensors axially spaced along the pipe or the at least one tube.

28. The method of claim 26, wherein the at least one sensor is an array of sensors having at least 4, 5, 6, 7, 8, 9, 10, 11, 12, 13, 14, 15, or 16 sensors axially spaced along the pipe or the at least one tube.

29. The method of claim 26, wherein the at least one sensor includes a pressure sensor, ported pressure sensor, ultrasonic sensor, or ported ultrasonic sensor.

30. The method of claim 26, wherein the at least one sensor is an array of sensors having at least two sensors axially spaced along the pipe or the at least one tube.

31. The method of claim 30, wherein the array of sensors are disposed on non-vibrating portions of the at least one vibratable tube.

32. The method of claim 30, wherein the array of sensors includes strain based sensors to measure acoustic pressures in the pipe or the at least one tube.

33. The method of claim 32, wherein the acoustic pressure is a one dimensional acoustic wave propagating axially through the fluid in the pipe or the at least one tube.

34. An apparatus for measuring mass flow rate of a fluid flowing in a pipe; the system comprising:
  a meter having at least two vibratable tubes wherein the fluid flows therethrough, the meter providing a phase signal indicative of a phase difference between the at least two vibratable tubes;
  a device having at least one sensor disposed at the pipe or the at least one tube to measure the speed of sound propagating through the fluid, the device providing at least one of an SOS signal indicative of the speed of sound propagating through the fluid; and
  a processing unit to determine a mass flow rate signal indicative of the mass flow rate of a non-gaseous portion of the fluid in response to the phase signal and the SOS signal.

35. The apparatus of claim 22 wherein the SOS signal is used to determine a GVF signal indicative of a gas volumetric fraction (GVF) of the fluid.

36. The apparatus of claim 22, wherein the phase signal is used to determine the mass flow rate of the aerated fluid.

37. The apparatus of claim 22, wherein the at least one sensor includes a pressure sensor, ported pressure sensor, ultrasonic sensor, or ported ultrasonic sensor.

38. The apparatus of claim 22, further includes a pressure sensor to provide a pressure signal indicative of the pressure of the fluid, and
  wherein the processing unit determines a mass flow rate signal indicative of the mass flow rate of the non-gaseous portion of the aerated fluid in response to the phase signal, the pressure signal, and the SOS signal.

39. The apparatus of claim 22, wherein the processing unit determines a mass flow rate signal indicative of the mass flow rate of the non-gaseous portion of the aerated fluid in response to the phase signal, the SOS signal, and a pressure signal indicative of the pressure of the fluid.

40. The apparatus of claim 22, wherein the meter is a coriolis meter.

41. The apparatus of claim 22, wherein the at least one sensor is an array of sensors having at least three sensors axially spaced along the pipe or the at least one tube.

42. The apparatus of claim 22, wherein the at least one sensor is an array of sensors having at least 4, 5, 6, 7, 8, 9, 10, 11, 12, 13, 14, 15, or 16 sensors axially spaced along the pipe or the at least one tube.

43. The apparatus of claim 22, wherein the at least one tube of the meter is bent or straight.

44. The apparatus of claim 22, wherein the device provides at least one of the SOS signal, a GVF signal indicative of the gas volume fraction of the fluid and a reduced frequency signal indicative of the reduced frequency of the fluid; and
  wherein the processing unit determines the mass flow rate signal indicative of the mass flow rate of the non-gaseous portion of the fluid in response to at least the phase signal, and at least one of the SOS signal, the GVF signal and the reduced frequency signal.

45. The apparatus of claim 22, wherein the at least one sensor is an array of sensors having at least two sensors axially spaced along the pipe or the at least one tube.

46. The apparatus of claim 35, wherein the array of sensors are disposed on non-vibrating portions of the at least one vibratable tube.

47. The apparatus of claim 35, wherein the array of sensors includes strain based sensors to measure acoustic pressures in the pipe or the at least one tube.

48. The apparatus of claim 45, wherein the acoustic pressure is a one dimensional acoustic wave propagating axially through the fluid in the pipe or the at least one tube.

49. A method of measuring mass flow rate of an aerated fluid flowing in a pipe; the method comprising:
  providing a phase signal indicative of the phase difference between at least two vibratable tubes;
  providing an SOS signal indicative of the speed of sound propagating through the fluid; and
  determining a mass flow rate signal indicative of the mass flow rate of the non-gaseous portion of the aerated fluid in response to the phase signal and the SOS signal.

50. The method of claim 36, wherein the at least one tube of the meter is bent or straight.

51. The method of claim 36, further includes providing at least one of the SOS signal, a GVF signal indicative of the gas volume fraction of the fluid and a reduced frequency signal indicative of the reduced frequency of the fluid; and
  determining the mass flow rate signal indicative of the mass flow rate of the non-gaseous portion of the fluid in response to at least the phase signal, and at least one of the SOS signal, the GVF signal and the reduced frequency signal.

52. The method of claim 36, wherein the meter is a coriolis meter.

53. The method of claim 36, further includes determining the mass flow rate of the aerated fluid in response to the phase signal.

54. The method of claim 36, further includes determining a GVF signal indicative of a gas volumetric fraction (GVF) of the fluid in response to the SOS signal.

55. The method of claim 36, wherein the determining the mass flow rate signal further includes determining the mass flow rate signal indicative of the mass flow rate of the non-gaseous portion of the aerated fluid in response to the phase signal, the SOS signal, and a pressure signal indicative of the pressure of the fluid.

56. The method of claim 52, further includes measuring the pressure of a fluid.

57. The method of claim 36, wherein the providing an SOS signal includes using a at least one sensor disposed at the pipe or the at least one tube to determine the speed of sound propagating through the fluid.

58. The method of claim 49, wherein the at least one sensor is an array of sensors having at least three sensors axially spaced along the pipe or the at least one tube.

59. The method of claim 49, wherein the at least one sensor is an array of sensors having at least 4, 5, 6, 7, 8, 9, 10, 11, 12, 13, 14, 15, or 16 sensors axially spaced along the pipe or the at least one tube.

60. The method of claim 49, wherein the at least one sensor includes a pressure sensor, ported pressure sensor, ultrasonic sensor, or ported ultrasonic sensor.

61. The method of claim 49, wherein the at least one sensor is an array of sensors having at least two sensors axially spaced along the pipe or the at least one tube.

62. The method of claim 54, wherein the array of sensors are disposed on non-vibrating portions of the at least one vibratable tube.

63. The method of claim 54, wherein the array of sensors includes strain based sensors to measure acoustic pressures in the pipe or the at least one tube.

64. The method of claim 61, wherein the acoustic pressure is a one dimensional acoustic wave propagating axially through the fluid in the pipe or the at least one tube.

* * * * *